United States Patent [19]

Cereda et al.

[11] Patent Number: 6,002,009

[45] Date of Patent: Dec. 14, 1999

[54] DI-SUBSTITUTED 1,4-PIPERIDINE ESTERS AND AMIDES HAVING 5-HT4 ANTAGONISTIC ACTIVITY

[75] Inventors: Enzo Cereda, Novi Ligure; Maura Bignotti, Milan; Vincenzo Martino, Induno Olana; Giovanni Battista Schiavi, Asola; Angelo Sagrada, Milan, all of Italy

[73] Assignee: Boehringer Ingelheim Italia, S.p.A., Firenze, Italy

[21] Appl. No.: 08/913,425

[22] PCT Filed: Mar. 4, 1996

[86] PCT No.: PCT/EP96/00903

§ 371 Date: Jan. 14, 1998

§ 102(e) Date: Jan. 14, 1998

[87] PCT Pub. No.: WO96/28424

PCT Pub. Date: Sep. 19, 1996

[30] Foreign Application Priority Data

Mar. 14, 1995 [IT] Italy .................................. MI95A0491

[51] Int. Cl.⁶ ...................... C07D 401/12; C07D 211/28; C07D 211/66; C07D 211/32

[52] U.S. Cl. .......................... 546/199; 546/199; 546/200; 546/201; 546/234; 546/229; 546/230; 546/231; 546/232; 546/233; 546/235

[58] Field of Search ...................................... 546/199, 201, 546/234, 200, 229–235

*Primary Examiner*—Alan L. Rotman
*Assistant Examiner*—Rita Desai
*Attorney, Agent, or Firm*—R. P. Raymond; M-E. M. Devlin; A. R. Stempel

[57] ABSTRACT

Pharmacologically active novel esters and amides of di-substituted 1,4 piperidine as 5-HT$_4$ antagonists of formula (I)

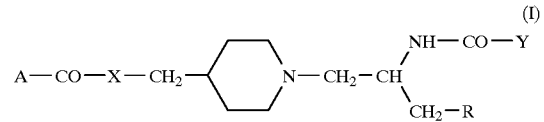

wherein A, X, Y and R have the meanings specified in the description, and a process for their preparation, are disclosed.

8 Claims, No Drawings

DI-SUBSTITUTED 1,4-PIPERIDINE ESTERS AND AMIDES HAVING 5-HT4 ANTAGONISTIC ACTIVITY

CROSS REFERENCE

This is a S371 of PCT/EP96/00903 filed Mar. 3, 1996.

The present invention refers to novel pharmacologically active derivatives of di-substituted 1,4-piperidine, the processes for their preparation and the pharmaceutical compositions containing them.

The novel compounds, object of the present invention, have a high affinity and specificity for 5-HT$_4$ serotoninergic receptors. They are able to inhibit, either at central or peripheral level, those effects mediated by the activation of this receptor subtype. Therefore, the compounds, object of the present invention, may be defined novel antagonists "in vitro" and "in vivo" of 5-HT$_4$ receptors. 5-HT$_4$ receptors belong to the numerous family of serotoninergic receptors and they are among those more recently discovered, pharmacologically characterized and cloned. After the first identification in discrete areas of guinea-pig CNS [Dumuis et al.; Mol. Pharmacol. (1988), 34, 880; Bockaert et al.; Trends, Pharmacol. Sci. (1992) 13, 141] the 5-HT$_4$ serotoninergic receptors have been localized also in other districts, either central or peripheral (ileum, atrium, esophagus, colon, urinary bladder and adrenal glands) of different species, including humans. [Craig et al.; Brit. J. Pharmacol. (1989) 96, 246 P; Craig et al.; J. Pharmacol. Exp. Ther. (1990) 352, 1378; Kauman et al.; Brit. J. Pharmacol. (1989), 98, 664 P; Hoyer et al.; Pharmacological Reviews (1994), 46, 157]. The presence of these receptors in different organs and tissues, make it possible that compounds able to block the effects of their hyperstimulation, may be advantageously used in the treatment and in the prophylaxis of different pathological situations.

Thus for example, since the stimulation of 5-HT$_4$ atrial cardiac receptors, besides causing inotropic and chronotropic positive effects, is responsible for arrhythmias observed in some experimental conditions [Kauman et al.; Naunyn-Schmiedeberg's Arch Pharmacol, (1994) 349, 331], antagonists to these receptors may be used in the specific treatment of cardiac rhythm disorders, such as atrial fibrillation and other types of arrhythmias. In the gastro-intestinal tract since the 5-HT$_4$ receptors mediate the prokinetic and secretory action of serotonin [Kilbinger et al; Naunyn-Schmiedeberg's Arch. Pharmacol. (1992) 345, 270; Burleigh; Eur. J. Pharmacol. (1991), 202, 277], it can be suggested the use of 5-HT$_4$ antagonists in the treatment of disorders connected to an altered intestinal motility or secretion such as I.B.S. (irritable bowel syndrome), more particularly in those forms of I.B.S. combined to diarrhoic states. The presence of 5-HT$_4$ receptors in central nervous system either in rat or in humans is not ubiquitary but limited to defined areas [Waeber et al.; Neuro Report (1993), 4, 1239; Monferini et al.; Life Sci. (1993), 52, 61] such as hippocampus, frontal cortex, basal ganglia and limbic structures. Compounds able to control an altered stimulation of the 5-HT$_4$ receptors in central nervous system may therefore be used in the psychiatric and neurological fields such as the therapeutical treatment of anxiety, depression, psychosis, cognitive disorders, motility disorders and migraine. Moreover, since it has been described [Panocka et al.; Pharmacol. Biochem. Behav. (1995) 52, 255] that 5-HT$_4$ receptors partially mediate the effect of 5-HT in controlling the ethanol intake, 5-HT$_4$ antagonists might be useful in the treatment of alcohol abuse. 5-HT$_4$ receptors are also involved in the control of other functions of the genitourinary and adrenal glands system, where they seem to mediate the release of steroidal hormones [Lefebre et al.; Neuroscience, (1992), 47, 999]. Consequently, pathologies characterized by an altered secretion of hormones or urinary incontinence might be also treated with compounds able to block the S-HT$_4$ receptors.

WO 94/08965 describes N-alkylpiperidinyl-4-methyl carboxylic esters/amides of condensed ring systems having 5-HT$_4$ antagonist activity. WO 93/18027 describes 5-HT$_4$ receptor antagonists derived from a heterocyclic nucleus including a benzimidazolone groupment, which is in our compounds only a generic substituent. EP 501.322 describes 3-piperidinylmethylcarboxylate substituted indoles which are antagonists of 5-hydroxytriptamine (5-HT). J. Med. Chem., 1993, 36, 4121-4123 describes (1-butyl-4-piperidinyl)methyl 8-amino-7-chloro-1,4-benzodioxane-5-carboxylate which is a quartenary salt.

It has now been found, and this is the object of the present invention, a novel class of compounds which possess a high affinity and selectivi-ty for the 5-HT$_4$ receptor and can be therefore used in the treatment of the disorders of cardiac rhythm, and intestinal motility such as I.B.S., anxiety, depression, psychoses, cognitive disorders, motility disorders, alcohol abuse and migraine.

The present invention relates to compounds of general formula (I)

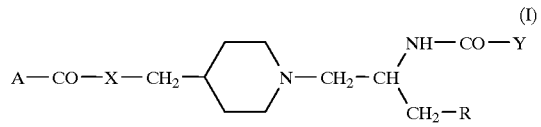

(I)

wherein

A represents a group selected from
substituted phenyl of structure

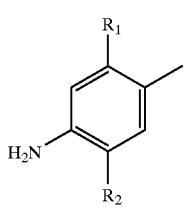

(a)

in which R$_1$ is C$_{1-3}$ alkoxy and R$_2$ is halogen;
bi- or tricyclic heterocycle selected from

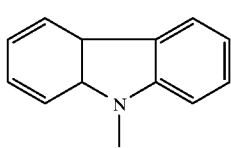

(b)

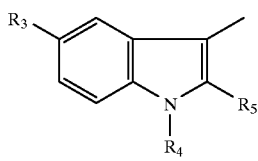

(c)

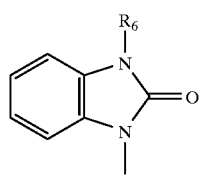

(d)

in which $R_3$ is hydrogen or halogen, $R_4$ is hydrogen or $C_{1-3}$ alkyl, $R_5$ is hydrogen or $C_{1-3}$ alkoxy, $R_6$ is hydrogen or a linear or branched $C_{1-6}$ alkyl;

X represents oxygen or NH;

Y represents a group of formula —$OR_7$ or $NHR_7$, wherein $R_7$ is $C_{1-3}$ alkyl, aryl or aralkyl;

R represents hydrogen, phenyl, hydroxy, benzyloxy, methylthiomethyl, 3-indolyl, methoxycarbonyl or carbamoyl;

and acid addition salts thereof with pharmacologically acceptable acids.

In the present specification, the term $C_{1-3}$ alkyl denotes a linear or branched chain such as methyl, ethyl, n-propyl or i-propyl. The term halogen means fluorine, chlorine, bromine and iodine. Preferred halogens are fluorine, chlorine, bromine, particularly fluorine, chlorine. The term $C_{1-3}$ alkoxy means methoxy, ethoxy or propoxy. When in the compounds of formula (I) $R_6$ represents a linear or branched $C_{16}$ alkyl, it may be, for example, methyl, ethyl, n-propyl, i-propyl, butyl, pentyl, hexyl, 2-methylpentyl and the like. When $R_7$ represents aryl, it may be, for example, phenyl. When $R_7$ represents aralkyl, it may be, for example, benzyl.

The compounds of general formula (I) have one asymmetric carbon atom and therefore can exist as optically active enantiomers having R or S configuration, or as racemic mixture. Even though in the examples the compounds are described and identified as single R or S enantiomers, it is to be understood that the invention relates to all the optical isomers as well as the racemic mixtures thereof.

The compounds of general formula I may be, for example, prepared by the following processes which are a further object of the present invention.

The compounds of formula (I), where X represents oxygen and A, R and Y are as hereinbefore defined, can be prepared according to the scheme 1, hereinafter reported.

SCHEME 1

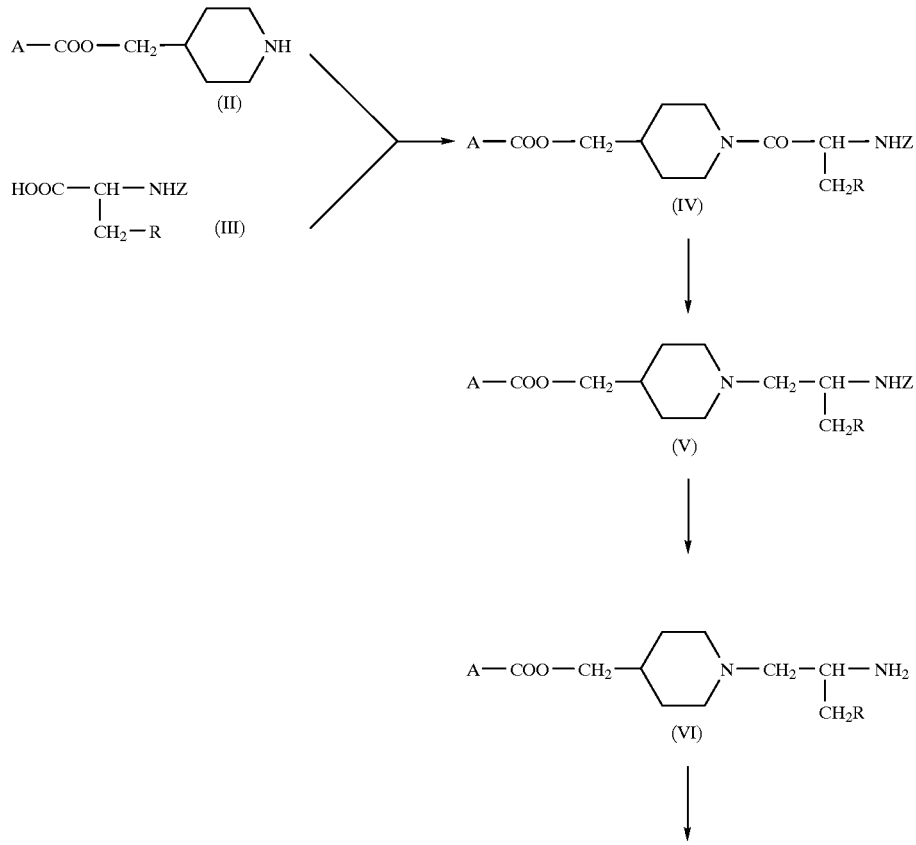

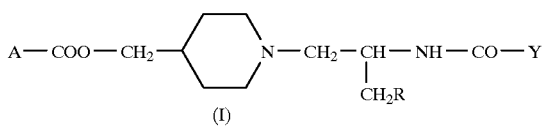

The intermediate amines of formula (VI), where A is as above defined and R represents hydrogen, phenyl, methylthiomethyl and 3-indolyl, are reacted with isocyanates of formula $R_7NCO$ or with chloroformates of formula $R_7O COCl$ where $R_7$ is as above defined. The reaction for the preparation of the ureas is carried out in a solvent selected from toluene, tetrahydrofuran, ethanol, methanol, preferably ethanol, at a temperature ranging from 0° C. to the reflux temperature of the solvent, preferably at room temperature.

For the preparation of the carbamates the reaction is carried out in an inert solvent such as tetrahydrofuran, diethyl ether or chloroform, preferably tetrahydrofuran in the presence of an acid acceptor such as pyridine or triethylamine at a temperature ranging from 0° C. to the reflux temperature of the solvent, preferably at room temperature.

In the particular case, when R represents a hydroxy group, the compounds of formula (I) may be prepared from the same precursors of formula (VI), in which A is as above defined and R represents a precursor of the hydroxy functionality such as the benzyloxy group. In this case, the transformation into ureido or carbamoyl derivatives, carried out according to the above described procedures and methods, is followed by the deprotection of the protected hydroxy group. There are several known methods for the deprotection of 0-benzylalcohols (see example "Protective Groups in Organic Synthesis" of T. W. Greem P. G. M. Wutz John Wiley, 1991, page 10–142). Particularly advantageous are the reduction processes with hydrogen or with its precursors such as cyclohexene or ammonium formate in the presence of suitable catalysts, preferably Pd/C. In another particular case, when R represents a carbamoyl group, the compounds of formula (I) may be prepared from the same precursors (VI) in which A is as above defined and R represents a carbamoyl precursor group, such as alkoxycarbonyl, preferably methoxycarbonyl. In this case the transformation into urea and carbamate derivatives, performed according to the procedures already described, is followed by an ammonolysis process with gaseous ammonia, introduced in the reaction mixture containing a protic or aprotic polar solvent, preferably methanol or acetonitrile at a temperature ranging from 0° C. to 30° C.

The intermediates of formula (VI) may be prepared from the precursors of formula (V) where A and R are as above defined and Z represents a suitable amino-protecting group, such as t-butoxycarbonyl or benzyloxycarbonyl, according to the traditional deprotecting methods (for example "Protective Group in Organic Synthesis" of T. W. Green and P. G. M Wuts, Ed.

John Wiley, 1991; page 309–405) conveniently selected according to the protecting group itself and to the other functional groups present in the substrate. For instance, t-butoxycarbonyl group may be easily removed by reacting the compound with anhydrous gaseous hydrochloric acid, in the presence of an apolar inert solvent such as diethyl ether or ethyl acetate at a temperature between –10° C and room temperature, preferably about 0° C.

The compounds of formula (V) may be prepared from the precursors of formula (IV) in which A, R and Z are as above defined, by known selective reduction processes conveniently selected from those which possess an high reactivity towards the amido group to be reduced, coupled with an inactivity toward other functionalities present in these intermediates (IV), above all carboxylic esters and carbamates. Particularly advantageous is the method based on borane complex in tetrahydrofuran at a temperature ranging between room temperature and the reflux temperature of the solvent, preferably at 50° C.

The compounds of formula (IV) may be prepared by reacting esters of formula (II), in which A is as above defined, with acidic intermediates of formula (III) where R and Z are as above defined. The compounds of formula (III) are amino acids protected at the nitrogen atom and they are commercialy available in the D or L absolute configuration. The process is carried out in a polar or apolar solvent, preferably tetrahydrofuran, after the activation of the amino acid carboxylic group, for instance by means of 1,1-carbonyldiimidazole.

The compounds of formula (I) wherein X is oxygen, A represents benzimidazolone (d), in which $R_6$ is as above defined, or indole (c); where $R_3$, $R_4$, $R_5$ and Y are as above defined, are better specified in the formulae (Id) and (Ic) respectively, and may be prepared according to the scheme 2, hereinafter reported.

SCHEME 2

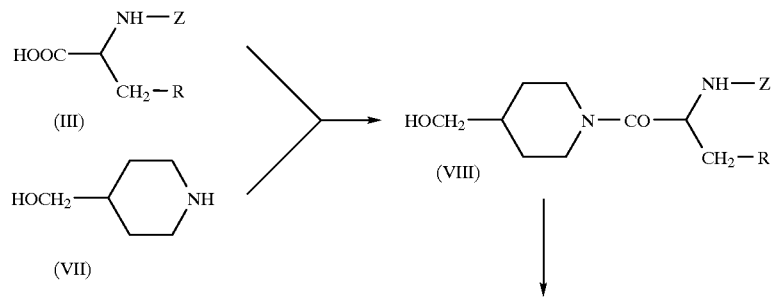

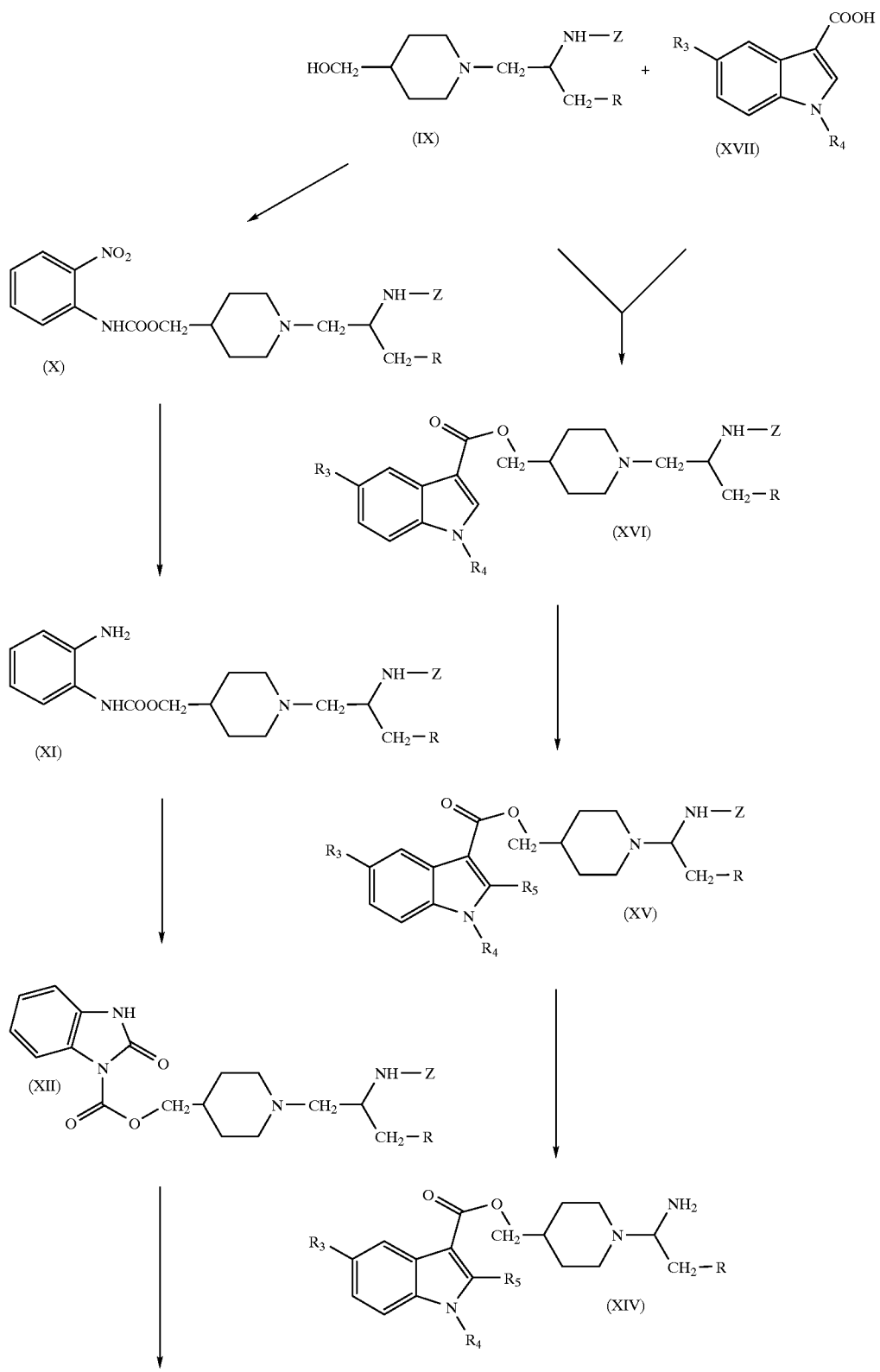

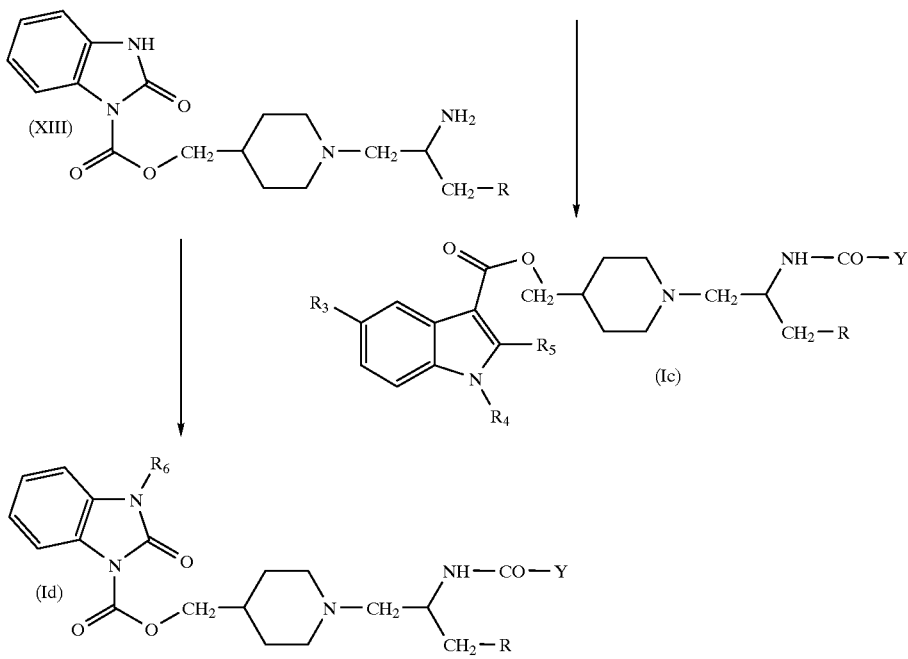

The intermediate amines of formula (XIII) in which R is hydrogen, phenyl, methylthiomethyl and 3-indolyl are converted into ureas or carbamates of formula (Id) by reaction with isocyanates $R_7$ NCO or chloroformates of formula $R_7O$ COCl according to the already described procedures. In the particular case, in which $R_6$ is different from hydrogen, the resulting compounds are further alkylated by means of an alkylating agent of formula $R_6$ Q, where Q represents a halogen atom, preferably chlorine or bromine, in the presence of an activating agent such as NaH, Na $NH_2$, KOH or NaOH, preferably NaH. The used solvent is generally an apolar or polar inert solvent, preferably tetrahydrofuran or dimethylformamide. The reaction temperature ranges from 10° C. to 80° C., preferably at room temperature. The intermediates of formula (XIII) may be prepared from the precursors of formula (XII), where R and Z are as above defined according to the traditional methods for deprotection of the amino functionality.

The compounds of formula (XII) may be obtained by cyclization of the compounds of formula (XI) in which R and Z are as already defined, by phosgene or its safer derivatives such as diphosgene or triphosgene, or carbonyl diimidazole in inert solvents such as tetrahydrofuran, ether, methylene chloride, preferably tetrahydrofuran. The reaction temperature may range from 0° C. to 60° C., preferably 40° C.

The compounds of formula (XI) may be prepared by reduction of nitro derivatives (X) where R and Z are as above defined, using suitable reagents and methods which do not affect the other functionalities present in the compounds and represented by Z and R. Particularly advantageous is the use of Sn $Cl_2.2H_2O$, as reducing agent, in an alcoholic solvent, such as methanol or ethanol, optionally containing water, preferably EtOH 95%. The reaction temperature ranges from 40° C. to the reflux temperature of the solvent, preferably 70° C.

The compounds of formula (X) may be prepared by reacting an aminoalcohol of formula (IX), where R and Z are as above defined, with o-nitrophenyl isocyanate in an inert solvent such as tetrahydrofuran, dioxane and toluene, preferably tetrahydrofuran, at a temperature ranging from room temperature to the reflux temperature of the solvent, preferably at 60° C.

The compounds of formula (IX) may be prepared from a precursor alcohol of formula (VIII), where R and Z are as above defined, according to the already mentioned selective reduction processes which are highly specific for the amido group, for example the borane complex in tetrahydrofuran, as above described.

The compounds of formula (VIII) may be obtained by reacting 4-hydroxymethylpiperidine (VII) with the already mentioned amino acid with D or L configuration, conveniently protected at the nitrogen atom (III). This process is carried out in an apolar or polar solvent, preferably tetrahydrofuran, after a suitable activation of the carboxylic functionality of the amino acid, by means of 1,1-carbonyldiimidazole. According to a further option, when in the compounds of formula (I) X is still oxygen and A represents indole (c), where $R_3$, $R_4$ and $R_5$ are as above defined, they are better identified in the formula I (c) and may be prepared as specified in the scheme 2. The intermediates of formula (XIV), where R, $_3$, $R_4$ and $R_5$ are as above defined, are transformed into the compounds (Ic) according to the previously described processes using isocyanates of formula $R_7$ NCO or chloroformates of formula $R_7OCOCl$, wherein $R_7$ is as above defined.

The intermediate amines (XIV), in turn, are obtained from precursors (XV), where $R_3$, $R_4$, $R_5$, R and Z are as above defined according to the already described deprotecting procedures of the amino functionality.

The intermediates (XV) in which $R_5$ is $C_1$–$C_3$ alkoxy may be prepared from precursors of formula (XVI) where $R_3$, $R_4$, R and Z have the above mentioned meanings, according to an alkoxylation process. At first, an oxidizing agent, such as N-chlorosuccinimide, in an inert halogenated solvent, such as methylene chloride or chloroform, activates the indolyl nucleus; then the process is completed by the use of a suitable alkylalcohol such methanol or ethanol. Both the process phases are carried out at a temperature ranging between 0° C. and 50° C., preferably at room temperature.

The compounds (XVI) may be obtained by reacting an indolcarboxylic acid of formula (XVII), where $R_3$ and $R_4$ are as above defined, with an aminoalcohol of formula (IX) where R and Z are as above described. The esterification process is carried out by activating the carboxylic function by the use of an anhydride, for example trifluoroacetic anhydride and methanesulfonic acid at a temperature lower than the room temperature, preferably between 0° and −5° C. The process is completed by adding the alcoholic component and increasing the in which $R_5$ is $C_1$–$C_3$ alkoxy temperature until 50°–60° C. The used solvent is generally a halogenated solvent selected from chloroform and methylene chloride.

The compounds of formula (I), wherein X is NH and A, R and Y are as above defined, may be prepared with synthetic steps, as reported in the scheme 3.

SCHEME 3

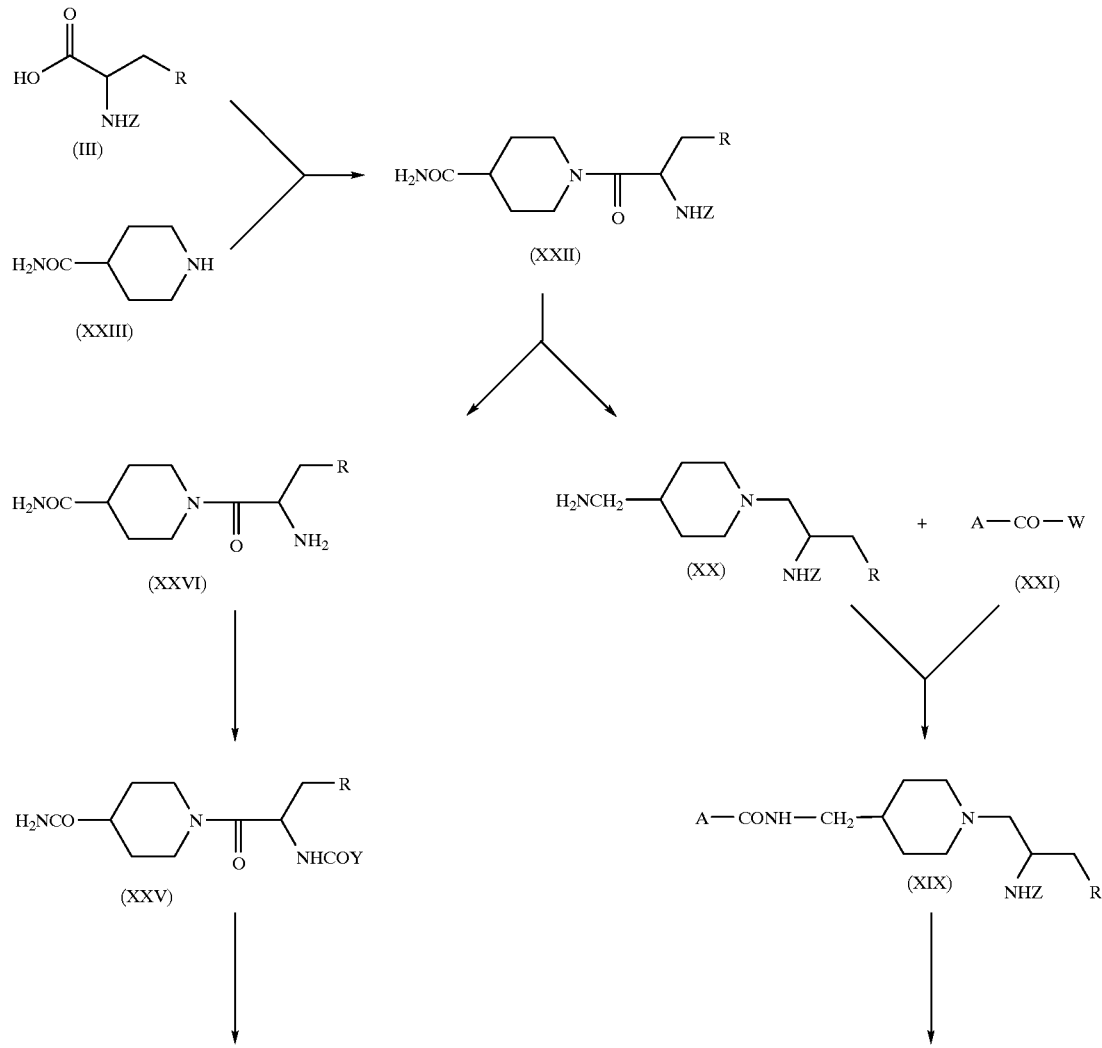

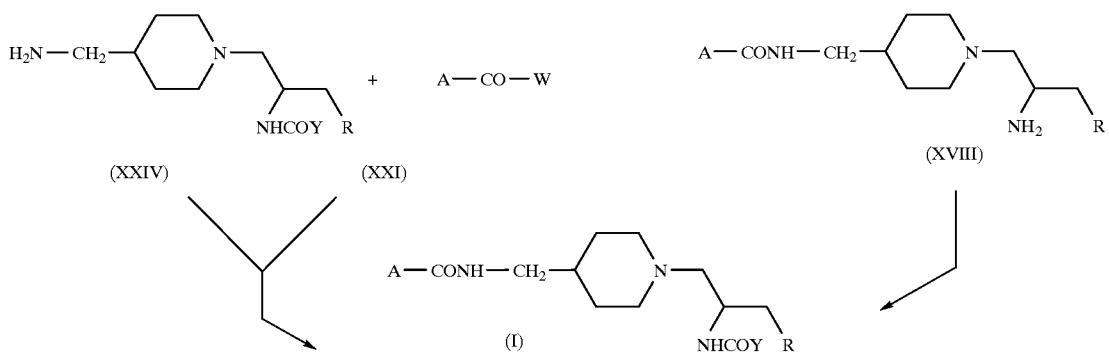

The intermediate amines of formula (XVIII) where A is as above defined and R represents hydrogen, phenyl, methylthiomethyl and indolyl are reacted with isocyanates of formula R$_7$NCO or with chloroformates R$_7$OCOCl where R$_7$ is as above defined. The used procedures are similar to those previously described.

In a particular case, when R represents a hydroxy group, the compounds of formula (I) may be prepared from the same precursors of formula (XVIII), where A is as above defined and R represents a precursor of a hydroxyl group such as benzyloxy group. In this case the transformation into urea or carbamate derivatives, performed as previously described, is followed by the deprotection of the hydroxy functionality, as above specified. In another particular case, when R represents a carbamoyl group, the compounds of formula (I) may be prepared from the same precursors of formula (XVIII), in which A is as above defined and R represents a precursor of a carbamoyl group, such as alkoxycarbonyl, preferably methoxycarbonyl. The conversion into urea or carbamate derivatives is followed by an amonolysis process, as already described.

The intermediates of formula (XVIII) may be prepared from the precursors of formula (XIX) where A and R are as above defined and Z represents a suitable amino-protecting group, such as t-butoxycarbonyl or benzyloxycarbonyl, according to the already described deprotection methods.

The compounds of formula (XIX) may be prepared by reacting amines of formula (XX), where R and Z are as above defined, with compounds of formula (XXI), where W is a suitable leaving group such as chlorine or imidazole. The process is performed in an inert solvent such as diethyl ether, tetrahydrofuran, methylene chloride, chloroform, toluene, preferably tetrahydrofuran in the presence of an organic base such as triethylamine, 1,8-diazabicyclo [5.4.0]-7-undecene (DBU) at a temperature ranging from 10° C. and the reflux temperature of the solvent, preferably 40° C.

The intermediates of formula (XXI), in turn, may be obtained from commercially available intermediates or prepared according to processes known in literature, by reaction with phosgene or better with their derivatives such as trichloromethyl chloroformates or bis (trichloromethyl) carbonate in an inert solvent such as toluene or tetrahydrofuran at a temperature ranging from 0° to 70° C.

The compounds of formula (XX) may be obtained from the intermediates of formula (XXII), where R and Z are as above defined, according to the above described selective reduction processes such as the use of borane complex in tetrahydrofuran. In the particular case, in which in the compounds of formula (XX) R is a carbamoyl group and Z is as above defined, they may be obtained from the same compounds of formula (XXII) where Z is as above defined and R represents an alkoxycarbonyl group such as methoxycarbonyl. The reduction process is followed by an amonolysis reaction, carried out using reagents and procedures already described.

The intermediates of formula (XXII) are prepared by reacting isonipecotamide (XXIII) with the intermediates of formula (III) where Z and R are as above defined. These compounds (III) are amino acids in which the amino function is protected by a Z group and they are commercially available in the D o L configuration. The process is performed in an apolar or polar inert solvent, preferably tetrahydrofuran, in the presence of a suitable activating reagent of the carboxylic function of the amino acids, such as 1,1-carbonyldiimidazole. Alternatively, the compounds of formula (I), included in the scheme 3, may be prepared by reacting amines of formula (XXIV), where R and Y are as already described, with the intermediates (XXI) in which A and W have the above mentioned meanings. The reaction is carried out in an inert solvent such as diethyl ether, tetrahydrofuran, methylene chloride, chloroform, toluene, preferably tetrahydrofuran, in the presence of an organic base such as triethylamine or DBU at a temperature ranging from 10° C. to the reflux temperature of the solvent, preferably 40° C. The intermediates (XXIV) are prepared from amides of formula (XXV), where R and Y have the described meaning, according to the already mentioned selective reduction processes, for example with the use of borane complex in tetrahydrofuran. The compounds of formula (XXV) may be prepared from the amines (XXVI), where R has the above mentioned meaning according to the previous described reactions with isocyanates or chloroformates of formula R$_7$NCO or R$_7$OCOCl respectively. Finally, the intermediates (XXVI) may be prepared by the precursors of formula XXII, in which Z and R have the above mentioned meaning, according to a suitable deprotection process of the amino function, as already specified.

The compounds of formula (I), object of the present invention, have, as above mentioned, an asymmetric carbon atom. Therefore, they may exist as two single optically active enantiomers having opposed configurations. The two enantiomeric forms of the final compounds (I) may be obtained starting from the precursor intermediates of formula (III) already possessing a predefined absolute R or S configuration and according to processes as described in the schemes 1, 2 and 3 according to procedure able to maintain the configuration at the chiral center. Alternatively, the same enantiomeric final forms (I) may be obtained according to conventional and well known methods which foresee the separation of the antipode forms, directly on the final compounds or on synthetic suitable intermediates having a basic functionality. These methods for the separation of the racemic mixture into the single enantiomers consist of single or repeated recrystallizations of the salts obtained from the final compounds or from basic intermediates with an optically active acid, such as d-camphorsulfonic, d- or l-tartaric and d- or l- O,O-ditoluoyl-tartaric acid. The utilized solvents are generally alcoholic solvents containing varying amounts of water.

The compounds of general formula (I), prepared according to the above described methods, may optionally be converted into the corresponding non-toxic, physiologically acceptable inorganic or organic acid addition salts, for example by conventional methods such as by reacting the compounds as bases, optionally dissolved in a suitable solvent with a solution of the corresponding acid in a suitable solvent. Examples of non-toxic physiologically acceptable acid addition salts are those formed with hydrobromic, hydrochloric, nitric, sulfuric, maleic, fumaric, citric, tartaric, methanesulphonic, p-toluenesulphonic, acetic, benzoic, succinic, gluconic, lactic, glycine, malic, muconic, glutamic, isethionic, phosphric, ascorbic or sulphamic acid. Particularly preferred acids are hydrochloric, hydrobromic, maleic, fumaric and methanesulphonic acids.

Preferred compounds according to the present invention, due to their better activity as $5-HT_4$ receptor antagonists, are those compounds of general formula (I), wherein A is the group (c) or (d), $R_3$ is halogen, $R_4$ is hydrogen or $C_{1-3}$ alkyl, $R_5$ is $C_{1-3}$ alkoxy, $R_6$ is a linear or branched $C_{1-6}$ alkyl, X is oxygen or NH, Y is $OR_7$ wherein $R_7$ is $C_{1-3}$ alkyl, aryl or aralkyl, R is hydrogen, hydroxy, benzyloxy or carbamoyl.

Pharmacology

The affinity of the compounds of formula (I) for $5-HT_4$ serotoninergic receptors was tested "in vitro" by receptor binding studies in the pig striatum, a tissue particularly rich in $5-HT_4$ receptors.

Receptor binding studies

Receptor binding studies on $5-HT_4$ receptor were carried out to determine the affinity of the test compounds.

Tissue preparation

Pig striatum was removed, cleaned and homogenized (w/v 1:70) with an Ultra-Turrax at maximal speed for 30 s, followed by use of a Potter-Elvehjem homogenizer (30 strokes) in 50 mM Hepes buffer, pH 7.4 and filtered through two layers of cheese-cloth.

Binding experiments

Binding curves for the different compounds were derived indirectly from competition experiments against 0.1 nM [$^3$H]-GR 113808.

A 1 ml aliquot of homogenate was incubated for 30 min at 37° C. in the presence of the marker ligand and different concentrations of the cold ligands.

The incubation was stopped by rapid filtration using an automatic apparatus (1H -110 Inotech). The filters (Inotech glass fibre filter, type G7) were then transferred to scintillation vials containing 4 ml of Filter Count (Packard) and the radioactivity present was counted by liquid scintillation spectrometry (Kontron Betamat V). Assays were carried out in triplicated and non specific binding was defined as the radioactivity bound or entrapped in the filter when the incubation medium contained 10 μM of BIMU 0001 (3-ethyl-2,3-dihydro-2-oxo-benzimidazole-1(3a-tropyl carboxamide). Non specific binding was about 10–15%. The inhibition constant (Ki) was calculated after correction for the radioligand occupancy shift according to the equation of Cheng and Prusoff (Biochem. Pharmacol. 22, 3099, 1973).

The results of receptor binding affinity for some compounds are reported in the following Table.

TABLE

| Affinity for the $5-HT_4$ receptor (pig striatum) | |
|---|---|
| Compound | Ki × $10^9$ M |
| 21 | 1.3 |
| 23 | 0.86 |
| 30 | 4.3 |
| 12 | 2.8 |
| 13 | 4.3 |
| 10 | 2.1 |
| 1 | 4.6 |
| 9 | 4.3 |
| 11 | 1.1 |
| 35 | 1.6 |
| 36 | 3.0 |
| 37 | 0.37 |
| 26 | 1.0 |
| 34 | 3.2 |
| 16 | 2.9 |
| 17 | 0.16 |
| 19 | 0.25 |

The ability of the compounds, herein described, to block $5-HT_4$ receptors was assessed "in vitro" by testing their activity in antagonizing the serotonin-induced relaxation of the tunica muscularis mucosa of rat esophagus, previously contracted by carbachol. The experiment was performed according to the described procedure [Baxter et al.; Naunyn-Schmiedeberg's Arch. Pharmacol. (1991), 343, 439].

All compounds, herein described, are able to antagonize $5-HT_4$ receptors with a good to high potency, showing $pA_2$ values generally higher, and in some cases much higher, than 7.

According to a further object of the present invention, there are provided pharmaceutical compositions for use according to the present invention comprising, as active ingredient, an effective amount of a compound of general formula (I) or physiologically acceptable acid addition salts in combination with one or more pharmaceutical carriers diluents or excipients.

The compositions may be formulated in a conventional manner, for the oral, parenteral, rectal or transdermal administration or in a form suitable for administration by inhalation or insufflation (either through the mouth or the nose).

For the oral administration, the pharmaceutical compositions may be, for example, in the form of tablets (including sustained release tablets), or capsules prepared in a conventional manner with pharmaceutically acceptable excipients such as corn starch, polyvinylpyrrolidone, lactose, microcrystalline cellulose, magnesium stearate, talc, potato starch, sodium lauryl sulphate. Liquid preparations for the oral administration may be, for example, in the form of solutions, syrups or suspensions which may be prepared in conventional manner with pharmaceutically acceptable additives such as sorbitol syrup, cellulose derivatives, lecithin, almond oil, methyl p-hydroxybenzoate, and if desired, buffer salts, flavouring, colouring and sweetening agents. Compounds of formula (I) may be formulated for the parenteral administration by injection, e.g. by bolus injection or continuous infusion. Compositions for injection may be presented in unit dosage form, e.g. in ampoules or in multi-dose containers. The compositions may be in the form of suspensions, solutions or emulsions in oily or aqueous vehicles. Alternatively, the active ingredient may be in powder form for constitution with a suitable vehicle, e.g. sterile apyrogenic water, before use.

For the rectal administration the pharmaceutical compositions may be, for example, in the form of suppositories containing conventional suppository bases, such as cocoa butter or other glycerides.

Besides the above described compositions, the compounds of formula (I) may also be formulated as a depot composition. Such long acting compositions may be administered by implantation (for example subcutaneously, transcutaneously or intramuscularly) or by intramuscular injection. Thus, these preparations may be, for example, formulated with suitable polymeric or hydrophobic materials or ion exchange resins.

In order to increase the solubility of the compounds of general formula (I) or their physiological acceptable salts, surfactants, non-ionic surfactants such as PEG 400, cyclodextrins, metastable polymorphs, inert absorbents such as bentonite may be incorporated. Furthermore, techniques such as preparation of, for example, eutectic mixtures and/or solid dispersions using mannitol, sorbitol, saccharose, succinic acid, or physical modified forms using water soluble polymers, PVP, PEG 4000–20000, may be employed.

The compositions are advantageously formulated in dosage unit: each dosage unit being adapted to supply a single dose of the active ingredient. Each dosage unit may conveniently contain 0.1 mg to 100 mg, preferably 1 mg to 20 mg of the active ingredient.

The following examples, including also the descriptions of the preparation of intermediates, illustrate some of the novel compounds according to the present invention; these examples are not to be considered in any way limitative of the scope of the invention itself.

Description 1
4-Amino-5-chloro-2-methoxy-benzoic acid (piperidin-4-yl) methyl ester a) 1,1-carbonyldiimidazole (0.8 g., 0.005 mol) was added to a solution of 4-amino-5-chloro-2-methoxy-benzoic acid (1 g, 5 mmol) in THF (20 ml) and the reaction mixture was stirred at room temperature for about 30 minutes. The solvent was evaporated and the residue was taken up in $H_2O$ and extracted into ethyl acetate (3×20 ml). The organic phases were collected, dried and evaporated to dryness. The obtained solid residue was dissolved in THF (10 ml) and dropped into a solution of 1-benzylpiperidin-4-yl-methanol [J. Med. Chem. (1992), 35, 4344], (1 g, 5 mmol) in THF (10 ml) and butyllithium (1.6 M in hexane; 3 ml), maintained at 0° C. The reaction mixture was further stirred at room temperature for 1 hour. The solvent was evaporated and the residue was taken up into $H_2O$ and extracted into ethyl acetate. The organic extracts were dried and evaporated to give the desired product as a pale yellow oil, (1.63 g).

b) a-chloroethylchloroformate (0.3 ml, 2.8 mmol) was dropped into a mixture of 4-amino-5-chloro-2-methoxy-benzoic acid (1-benzyl-piperidin-4-yl) methyl ester, (1 g., 2.6 mmol) and proton sponge (0.27 g., 1.3 mmol) in 1,2-dichloroethane (20 ml), maintained at 0° C. The mixture was further stirred at room temperature overnight. The reaction mixture was then poured into aqueous solution of 5% HCl and the organic layer, which separated, was washed with $H_2O$ dried and evaporated to dryness. The residue was taken up into $CH_3OH$ (20 ml) and heated at reflux temperature for 30 minutes. The solvent was evaporated to give the desired compound as hydrochloride salt, white solid (0.36 g.) M.p. 250–251° C.

According to the above described procedure the following product was prepared:

1-Methyl-indol-carboxylic acid (piperidin-4-yl) ester M.p. 227–239° C. (as hydrochloride salt).

Description 2
Carbazole-9-carboxylic acid (piperidin-4-yl)methyl ester a) Pyridine (7.2 ml; 0.090 mol) containing activated carbon (1.5 g.) was added to a solution of carbazole (10 g., 0.060 mol) in anhydrous toluene. After heating at 100° C., diphosgene (5.6 ml, 0.046 mol) was dropped in. The reaction mixture was stirred at 100° C. for 18 hours. The obtained pyridine salts were filtered off and the remaining solution was evaporated to dryness. 13 g. of a reddish-brown solid were obtained. M.p. 95–96° C.

b) Carbazole-9-carbonyl chloride (26 g., 0.108 mol) was added portionwise to a solution, obtained by dissolving 1-benzylpiperidin-4-yl-methanol (22.2 g., 0.108 mol) in anhydrous $CH_2Cl_2$ (700 ml), under stirring at room temperature for 48 hours. After this period, the solution was evaporated to dryness and the obtained raw solid was purified by chromatography (silica gel; eluent: $CH_2Cl_2/CH_3OH=96/4$). 30 g of a pink solid were obtained. M.p. 196–199° C. (as hydrochloride salt).

c) 10% Pd/C (15 g.) and, ammonium formate (10.8 g. 0.175 mol) were simultaneously added to a solution, obtained by dissolving carbazole-9-carboxylic acid (1-benzyl-piperidin-4-yl) methyl ester (15 g., 0.035 mol) in $CH_3OH$ (450 ml). The reaction mixture was refluxed for 40 minutes; the heating was interrupted and the reaction mixture was stirred while cooling to room temperature. The catalyst was filtered and the clear and colourless solution was evaporated to dryness. 9 g. of white solid were obtained. M.p. 240° C. dec. (hydrochloride salt).

Description 3
S(−)-4-Amino-5-chloro-2-methoxy-benzoic acid [1-(2-tert-butoxycarbonylamino-3-benzyloxypropionyl)-piperidin-4-yl]methyl ester 1,1-Carbonyldimidazole (5.3 g., 0.033 mol) was added to a solution of L—O—Bz serine N-t-Boc (9.7 g., 0.033 moli) in THF (100 ml) and the mixture was stirred at room temperature for 40 minutes. A solution of 4-amino-5-chloro-2-methoxy-benzoic acid (piperidin-4-yl) methyl ester (9.7 g., 0.033 mol) in THF (50 ml) was dropped and the reaction mixture was stirred overnight at room temperature. The solvent was evaporated to dryness and the residue was taken up in $H_2O$ and extracted into ethyl acetate. The organic extracts were collected, dried and evaporated to dryness. The obtained residue was purified by chromatography (silica gel; eluent: n-hexane/ethylacetate=4/6) to give the desired product as a pale yellow solid (10.47 g). $[a]^{20}_D=-0.97°$ (c=1% $CH_3OH$). According to the above described procedure the following products may be prepared: S(+)-4-Amino-5-chloro-2-methoxy-benzoic acid [1-(2-benzyloxycarbonyl-amino-3-phenyl-propionyl)-piperidin-4-yl]methyl ester $[a]^{20}_D=+8.48°$ (c=1% $CH_3OH$) S(+)-4-amino-5-chloro-2-methoxy-benzoic acid {1-[2-tert-butoxycarbonyl-amino-3-(1H-indol-3-yl)-propionyl] piperidin-4-yl} methyl ester $[a]^{20}_D=+21.28°$ (c=1% $CH_3OH$) S(−)-4-Amino-5-chloro-2-methoxy-benzoic acid [1-(2-tert-butoxycarbonyl-amino-4-methylthio-butiryl) piperidin-4-yl]methyl ester $[a]^{20}_D=-14.13°$ (c=1% $CH_3OH$) S(+)-1-Methyl-1-H-indol-3yl-carboxylic acid [1-(2-benzyloxycarbonyl-amino-3-phenyl-propionyl)piperidin-4-yl]methyl ester $[a]^{20}_D=+8.16°$ (c=1% $CH_3OH$) S(+)-Carbazole-9-carboxylic acid [1-(2-benzyloxy-carbonyl-amino-propionyl) piperidin-4-yl]methyl ester $[a]^{20}_D=+12.16°$ (c=1% $CH_3COOH$) M.p. 70° C. dec. S(+)-Carbazole-9-carboxylic acid [1-(2-benzyloxycarbonyl-amino-3-phenyl-propionyl)-piperidin-4-yl]methyl ester $[a]^{20}_D=+15.45°$ (c=1% $CH_3COOH$) M.p. 75° C. S(−)-Carbazole-9-carboxylic acid [1-(2-tert-butoxycarbonyl-amino-3- benzyloxy-propionyl)piperidin-4-yl3methyl ester $[a]^{20}{}_D=-2.13°$ (c=1% $CH_3OH$) M.p. 67–69° C. S(−)-Carbazole-9-carboxylic acid [1-( 2-(tert-butoxy-carbonyl-amino-3-methoxycarbonyl-propionyl)-piperidin-4-yl]methyl ester $[a]^{20}{}_D=-23.28°$ (c=1% $CH_3OH$). M.p. 76–78° C. S(+)-1-Methyl-1-indol-3-yl-carboxylic acid [1-(2-benzyloxycarbonyl-amino-3-phenyl-propionyl)piperidin-4-yl]-methyl ester $[a]^{20}{}_D=+8.16°$ (c=1% $CH_3OH$).

Description 4

S(−)-Carbazole-9-carboxylic acid [1-(2-benzyloxy-carbonyl-amino-3-phenyl-propyl)-piperidin-4-yl] methyl ester S(+)-carbazole-9-carboxylic acid [1-(2-benzyloxy-carbonyl-amino-3-phenyl-propionyl)-piperidin-4-yl] methyl ester (4 g., 7 mmol) dissolved in anhydrous THF (60 ml) was dropped to a 1M solution of borane complex (33 ml, 0.033 mol) in anhydrous THF (60 ml) heated at mild reflux. The solution was refluxed under stirring for 8 hours and then cooled at room temperature. The solvent was evaporated and the raw residue was purified by chromatography (silica gel; eluent: $CH_2Cl_2/CH_3OH=95/5$) to give a white solid (1.5 g.). $[a]^{20}{}_D=-3.36°$ (c=1% $CH_3COOH$). M.p. 200° C. dec. Analogously the following compounds may be prepared: S(+)-Carbazole-9-carboxylic acid [1-(2-benzyloxycarbonyl-amino-propyl)-piperidin-4-yl]methyl ester $[a]^{20}{}_D=+13.16°$ (c=1% $CH_3COOH$) R(+)-Carbazole-9-carboxylic acid [1-(2-t-butoxycarbonyl-amino-3-benzyloxy-propyl)-piperidin-4-yl]methyl ester $[a]^{20}{}_D=+9.58°$ (c=1% $CH_3COOH$). M.p. 170–172° C. (hydrochloride salt) S(−)-Carbazole-9-carboxylic acid (1-(2-t-butoxycarbonyl-amino-3-methoxycarbonyl-propyl)-piperidin-4-yl]methyl ester thick oil; $[a]^{20}{}_D=2.8°$ (c=1% $CH_3OH$) S-4-Amino-5-chloro-2-methoxy-benzoic acid [1-(2-t-butoxycarbonyl-amino-3-benzyloxy-propyl)piperidin-4-yl]methyl ester $[a]^{20}{}_D=-4.5°$ (c=1% $CH_3OH$) S(−)-4-Amino-5-chloro-2-methoxy-benzoic acid [1-(2-tert-butoxycarbonyl-amino-3-(1H-indol-3-yl)propyl]piperidin-4-yl}methyl ester $[a]^{20}{}_D=-2.67°$ (c=1% $CH_3OH$) S(+)-4-Amino-5-chloro-2-methoxy-benzoic acid [1-(2-tert-butoxycarbonyl-amino-3-methylthio-butyl)piperidin-4-yl]methyl ester $[a]^{20}{}_D=+9.94°$ (c=1% $CH_3OH$, as hydrochloride salt) S(+)-1-Methyl-1H-indol-3-yl-carboxylic acid [1-(2-benzyloxycarbonyl-amino-3-phenyl-propyl)-piperidin-4-yl]methyl, ester $[a]^{20}{}_D=+0.25°$ (c=1% $CH_3OH$) S-4-Amino-5-chloro-2-methoxy-benzoic acid [1-(2-tert-butoxycarbonyl-amino-3-phenyl-propyl)piperidin-4-yl)methyl, ester. $[a]^{20}{}_D=+6.2°$ (c=1% $CH_3OH$)

Description 5

S(+)-4-Amino-5-chloro-2-methoxy-benzoic acid {1-[2-amino-3-(1H-indol-3-yl)propyl]-piperidin-4-yl} methyl ester Anhydrous gaseous HCl was bubbled for 30 minutes into a solution of S(−)-4-amino-5-chloro-2-methoxy-benzoic acid {1-[2-tert-butoxycarbonyl-amino-3-(1H-indol-3-yl)propyl]-piperidin-4-yl]methyl ester (2 g, 3.5 mmol) in ethyl acetate (30 ml) cooled at 0° C. The solvent was evaporated obtaining a solid residue which, after crystallization with diethyl ether, gave the desired product as hydrochloride salt, white solid (1.8 g.). $[a]^{20}{}_D=+7.4°$ (c=1% $CH_3OH$, as hydrochloride salt). According to the above described procedure the following products may be prepared: S-4-Amino-5-chloro-2-methoxy-benzoic acid [1-(2-amino-3-benzyloxy-propyl)-piperidin-4-yl)methyl ester $[a]20_D=+7.3°$ (c=1% $CH_3OH$) S-4-Amino-5-chloro-2-methoxy-benzoic acid (1-(2-amino-3-phenyl-propyl)piperidin-4-yl]methyl ester $[a]^{20}{}_D=-5.5°$ (c=1% $CH_3OH$) R(+)-Carbazole-9-carboxylic acid [1-(2-amino-3-benzyloxy-propyl)-piperidin-4-yl] methyl ester, $[a]^{20}{}_D=+1.64°$ (c=1% $CH_3OH$) S(+)-Carbazole-9-carboxylic acid [1-(2-amino-3-methoxycarbonyl-propyl)-piperidin-4-yl]methyl ester $[a]^{20}{}_D=+2.63°$ (c=0.5% $CH_3OH$) R(+)-5-Fluoro-1H-indol-3-carboxylic acid [1-(2-amino-3-benzyloxypropyl)-piperidin-4-yl]methyl ester $[a]^{20}{}_D=+3.4°$ (c 1% $CH_3OH$) M.p. 150° C. (from ethyl acetate) R(+)-5-Fluoro-2-methoxy-1H-indole-3-carboxylic acid [1-(2-amino-3-benzyloxypropyl)-piperidin-4-yl]methyl ester $[a]^{20}{}_D=+1.55°$ (c=1% $CH_3OH$ as hydrochloride salt) M.p. 125–130° C. dec (as hydrochloride salt, from diethyl ether)

Description 6

S(+)-Carbazole-9-carboxylic acid [1-(2-amino-propyl)-piperidin-4-yl)methyl ester 10% Pd/C (0.82 g.) and ammonium formate (0.48 g, 7.65 mmol) was simultaneously added to a solution obtained by dissolving S(+)-carbazole-9-carboxylic acid [1-(2-carbobenzyloxyamino-propyl)-piperidin-4-yl]methyl ester (0.82 g., 1.53 mmol) in $CH_3OH$ (35 ml). The reaction mixture was refluxed for 40 minutes; the heating was interrupted and it was further stirred while cooling to room temperature. The catalyst was filtered and the clear and colourless solution was evaporated to dryness. 9.45 g. of white solid were obtained. $[a]^{20}{}_D=+26°$ (c=1% $CH_3OH$ as hydrochloride salt) M.p. 188–190° C. dec (as hydrochloride salt). Analogously the following compound was prepared: S(+)-Carbazole-9-carboxylic acid [1-(2-amino-3-phenyl-propyl)-piperidin-4-yl] methyl ester $[a]^{20}{}_D=+2.08°$ (c=1% $CH_3COOH$)

Description 7

S(+)-1-Methyl-1H-indol-3-carboxylic acid [1-(2-amino-3-phenyl-propyl)-piperidin-4-yl]methyl ester A suspension of S(+)-1-methyl-1H-indol-3-carboxylic acid [1-(2-CBZ-amino-3-phenyl-3-propyl)-piperidin-4-yl] methyl ester (3.3 g., 6.11 mmol) and 10% Pd/C (0.33 g.) in absolute $CH_3CH_2OH$ (35 ml) and diethyl ether containing 20% of HCl (1.1 ml) was stirred overnight in the presence of $H_2$ at room temperature and pressure. The catalyst was filtered and the solution was evaporated to dryness. The residue was crystallized from acetone to give the product as hydrochloride salt 2.5 g., $[a]^{20}{}_D=+30.1°$ (c=1% $CH_3OH$) M.p. 212–215° C. dec.

EXAMPLE 1

S(+)-4-Amino-5-chloro-2-methoxy-benzoic acid {1-[3-benzyloxy-2-(3-phenyl-ureido)-propyl]-piperidin-4-yl} methyl ester Phenylisocyanate (0.35 g., 3.2 mmol) was dropped into a solution of S-4-amino-5-chloro-2-methoxy-benzoic acid [1−2-amino-3-benzyloxy-propyl)-piperidin-4-yl]methyl ester (1.5 g., 3.2 mmol) in THF (20 ml) cooled at 0° C. and the reaction mixture was stirred at 0° C. for 30 minutes. The solvent was evaporated to dryness to give a raw product which, after chromatography (silica gel, eluent: EtAc/$CH_3OH=98/2$), gave the desired product as white foamy solid (1.6 g.). $[a]^{20}{}_D=+5.59°$ (c=1% $CH_3OH$). According to the above described procedure the following products may be prepared: S(+)-4-Amino-5-chloro-2-methoxy-benzoic acid (1-[3-benzyloxy-2-(3-ethyl-ureido)propyl]piperidin-4-yl} methyl ester $[a]^{20}{}_D=+5.08°$ (c=1% $CH_3OH$). R(+)-5-Fluoro-1H-indol-3-carboxylic acid {1-[2-(3-phenyl-ureido)-3-benzyloxypropyl]-piperidin-4-yl} methyl ester $[a]^{20}{}_D=+14.7°$ (c=1% $CH_3OH$). R(+)-Carbazole-9-carboxylic acid {1-[3-benzyloxy-2-(3-ethyl-ureido-propyl]-piperidin-4-yl} methyl ester $[a]^{20}{}_D=+11.88°$ (c=1% $CH_3OH$). S(+)-Carbazole-9-carboxylic acid {1-[3-methoxycarbonyl-2-(3- phenyl-ureido)-propyl]-piperidin-4-yl} methyl ester $[a]^{20}{}_D$=+10.9° (c=1% $CH_3OH$). S(+)-4-Amino-5-chloro-2-methoxy-benzoic acid {1-[2-(3-ethyl-ureido)-3-(1H-indol-3-yl) propyl] piperidin-4-yl} methyl, ester.

(Compound 1)

$[a]^{20}{}_D$=+13.25° (c=1% $CH_3OH$) M.p.=143°–145° C. (as hydrochloride salt, from diethyl ether) M.S. (C.I.)=543 m/e (M+H) Analysis: $C_{28}H_{37}Cl_2N_5O_4$

|  | C | H | N |
|---|---|---|---|
| Found % | 57.19 | 6.46 | 12.00 |
| Calc. % | 58.13 | 6.45 | 12.11 |

S(−)-4-Amino-5-chloro-2-methoxy-benzoic acid {1-[4-methylthio-2-(3-phenyl-ureido)-butyl]piperidin-4-yl} methyl ester.

(Compound 2)

$[a]^{20}{}_D$=−0.8° (c=1% $CH_3OH$) M.p.=121°–123° C. (as hydrochloride salt, from diethyl ether) M.S.=536 m/e [M+H]Analysis: $C_{26}H_{36}Cl_2N_4O_4S$

|  | C | H | N |
|---|---|---|---|
| Found % | 53.97 | 6.34 | 9.50 |
| Calc. % | 54.64 | 6.35 | 9.80 |

S(+)-Carbazole-9-carboxylic acid {1-[2-(3-phenyl-ureido)-propyl]-piperidin-4-yl} methyl ester (Compound 3)

$[a]^{20}{}_D$=+8.74° (c=1% $CH_3COOH$) M.p.=188°–190° C. (as hydrochloride salt, from diethyl ether) M.S. (C.I.)=485 m/e [M+H]Analysis: $C_2 H_{33}Cl N_4O_3$

|  | C | H | N |
|---|---|---|---|
| Found % | 66.18 | 6.20 | 10.38 |
| Calc. % | 66.85 | 6.38 | 10.75 |

S(+)-Carbazole-9-carboxylic acid {1-[2-(3-ethyl-ureido)-phenylpropyl]-piperidin-4-yl} methyl ester (Compound 4)

$[a]^{20}{}_D$=+0.76° (c=1% $CH_3COOH$) M.p.=95° C. (as hydrochloride salt, from diethyl ether) M.S. (C.I.)=513 m/e [M+H] Analysis: $C_{31}H_{37}Cl N_4O_4$

|  | C | H | N |
|---|---|---|---|
| Found % | 68.00 | 6.82 | 10.40 |
| Calc. % | 67.81 | 6.79 | 10.20 |

S(+)-1-Methyl-1H-indol-carboxylic acid {1-[2-(3-ethyl-ureido)-propyl]-piperidin-4-yl} methyl ester (Compound 5)

$[a]^{20}{}_D$=+11.02° (c=1% $CH_3OH$, as hydrochloride salt) M.p.=200–205° C. dec (as hydrochloride salt, from diethyl ether) M.S. (C.I.)=477 m/e [M+H] Analysis: $C_{28}H_{37}Cl N_4O_3$

|  | C | H | N |
|---|---|---|---|
| Found % | 65.50 | 7.32 | 10.95 |
| Calc. % | 65.55 | 7.27 | 10.92 |

EXAMPLE 2

R(+)-Carbazole-9-carboxylic acid [1-(2-ethoxycarbonyl-amino-3-benzyloxy-propyl)-piperidin-4-yl]methyl ester A solution, obtained by dissolving S(+)-carbazole-9-carboxylic acid [1-(2-amino-3-benzyloxy-propyl)-piperidin-4-yl)methyl ester (1 g., 1.84 mmol) in $CH_2Cl_2$ (30 ml) was cooled at 0° C. and then ethyl chloroformate (0.350 ml, 3.69 mmol) was dropped in. The reaction mixture was stirred under cooling for 15 minutes and then reaction mixture was stirred at room temperature for 6 hours. The solution was evaporated to dryness and the raw product was purified by chromatography (silica gel; eluent: $CHCl_3/CH_3OH$=98/2). 400 mg of semisolid product were obtained. The corresponding hydrochloride salt was obtained by bubbling gaseous HCl into a solution of the free base in AcOEt. $[a]^{20}{}_D$=+9.20 (c=1% $CH_3OH$).

Analogously the following products may be prepared: R(+)-5-Fluoro-2-methoxy-1H-indol-3-carboxylic acid [1-(2-benzyloxy carbonylamino-3-benzyloxypropyl)-piperidin- 4-yl] methyl ester. $[a]^{20}{}_D$=+1.20 (c=1% $CH_3OH$) S(−)-Carbazole-9-carboxylic acid [1-(2-ethoxycarbonyl-amino-3-methoxycarbonyl-propyl)-piperidin-4-yl]methyl ester. M.p.=85° C. $[a]^{20}{}_D$=−0.55 (c=1% $CH_3OH$) R(+)-5-Fluoro-1H-indol-3-carboxylic acid [1(2-ethoxycarbonyl-amino-3-benzyloxypropyl)-piperidin-4-yl]methyl ester. $(a]^{20}{}_D$=+6.90° (c=1% $CH_3OH$) S(−)-5-Fluoro-1-H-indol-3-carboxylic acid [1-(2-ethoxycarbonyl-amino-3-benzyloxypropyl)-piperidin-4-yl]methyl ester. $[a]^{20}{}_D$=−7.02° (c=1% $CH_3OH$) S(+)-Carbazole-9-carboxylic acid [1-(2-ethoxycarbonyl-amino)-3-phenyl-propyl)piperidin-4-yl] methyl ester.

(Compound 6)

$[a]^{20}{}_D$=+9.31° (c=1% $CH_3COOH$) M.p.=118° C dec. (as tartrate salt, from ethylacetate); M.S. (C.I)=514 m/e [M+H] Analysis: $C_{35}H_{41}N_3O_{10}$

|  | C | H | N |
|---|---|---|---|
| Found % | 62.92 | 6.33 | 6.13 |
| Calc. % | 63.34 | 6.23 | 6.33 |

S(+)-Carbazole-9-carboxylic acid [1-(2-ethoxycarbonyl-amino)-propyl)-piperidin-4-yl]methyl ester (Compound 7)

$[a]^{20}{}_D$+13.68° (c=1% $CH_3COOH$) M.p.=196–198° C. dec. (as hydrochloride salt, from ethyl acetate); M.S. (C.I.)= 438 m/e [M+H]Analysis: $C_{25}H_{32}Cl N_3O_4$

|  | C | H | N |
|---|---|---|---|
| Found % | 63.30 | 6.81 | 8.81 |
| Calc. % | 63.35 | 6.81 | 8.87 | ethoxycarbonyl-amino)-propyl]-piperidin-4-yl} methyl ester.

(Compound 8)

$[a]^{20}{}_D$=+8.21° (c=1% $CH_3OH$, as hydrochloride salt) M.p.=200–204° C. dec. (as hydrochloride salt, from diethyl ether); M.S. (C.I.)=478 m/e [M+H] Analysis: $C_{28}H_{36}Cl N_3O_4$

|  | C | H | N |
|---|---|---|---|
| Found % | 65.34 | 7.08 | 8.12 |
| Calc. % | 65.42 | 7.06 | 8.17 |

S(+)-4-Amino-5-chloro-2-methoxy-benzoic acid [1-(2-ethoxycarbonyl-amino-4-methylthio-butyl)-piperidin-4-yl] methyl ester.
(Compound 9)
$[a]^{20}_D$=+3.98° (c=1% $CH_3OH$, as hydrochloride salt) M.p.=151–153° C. dec. (as hydrochloride salt, from diethyl ether); M.S. (C.I.)=489 m/e [M+H] Analysis: $C_{22}H_{35}Cl_2N_3O_5S$

|  | C | H | N |
|---|---|---|---|
| Found % | 49.81 | 6.79 | 7.85 |
| Calc. % | 50.38 | 6.73 | 8.01 |

S(+)-4-Amino-5-chloro-2-methoxybenzoic acid {1-[2-benzyloxycarbonyl-amino-3-(1H-indol-3-yl)-propyl] piperidin-4-yl} methyl ester.
(Compound 10)
$[a]^{20}_D$=+0.58° (c=1% $CH_3OH$, as hydrochloride salt) M.p.=191–193° C. dec. (as hydrochloride salt, from diethyl ether); M.S. (C.I.)=606 m/e [M+H] Analysis: $C_{33}H_{38}Cl_2N_4O_5$

|  | C | H | N |
|---|---|---|---|
| Found % | 61.03 | 5.80 | 8.62 |
| Calc. % | 61.78 | 5.97 | 8.73 |

S(+)-4-Amino-5-chloro-2-methoxybenzoic acid [1-(2-benzyloxycarbonyl-amino-3-phenyl-propyl)-piperidin-4-yl] methyl ester
(Compound 11)
$[a]^{20}_D$=+1.57° (c=1% $CH_3OH$, as hydrochloride salt) M.p.=165–167° C. dec. (as hydrochloride salt as diethyl ether); M.S. (C.I.)=567 m/e [M+H] Analysis: $C_{31}H_{37}Cl_2N_3O_5$

|  | C | H | N |
|---|---|---|---|
| Found % | 60.85 | 6.14 | 6.86 |
| Calc. % | 61.79 | 6.19 | 6.97 |

S(−)-5-Fluoro-2-methoxy-1-H-indole-3-carboxylic acid 1 [(2-benzyloxycarbonyl-amino-3-phenyl)-propyl]-piperidin-4-yl-methyl ester
(Compound 40)
$[a]^{20}_D$=−1.2 (C=1% $CH_3OH$). M.p. 155–160° C. dec., as fumarate salt. M.S. (C.I.)=574 m/e [M+H] Analysis: $C_{33}H_{36}F\ N_3O_5$

|  | C | H | N |
|---|---|---|---|
| Found % | 63.90 | 5.86 | 6.12 |
| Calc. % | 64.43 | 5.85 | 6.09 |

R(+)-5-Fluoro-2-methoxy-1H-indole-3-carboxylic acid-1-[(2-benzyloxycarbonyl-amino-3-phenyl)-propyl]-piperidin-4-yl-methyl ester
(Compound 41)

$[a]^{20}_D$=+1.16 (C=1% $CH_3OH$). M.p. 154–158° C. dec., as fumarate salt. M.S. (C.I.)=574 m/e [M+H] Analysis: $C_{33}H_{36}F\ N_3O_5$

|  | C | H | N |
|---|---|---|---|
| Found % | 64.30 | 5.90 | 6.05 |
| Calc. % | 64.43 | 5.85 | 6.09 |

EXAMPLE 3

R(+)-Carbazole-9-carboxylic acid [1(2-ethoxycarbonyl-amino-3-hydroxy-propyl)-piperidin-4-yl]methyl ester
(Compound 12)
10% Pd/C (0.76 g.) and ammonium formate (400 mg., 6.5 mmol) were added simoultaneously to a solution obtained by dissolving S(+)-carbazole-9-carboxylic acid [1-(2-ethoxycarbonyl-amino-3-benzyloxy-propyl)-piperidin-4-yl] methyl ester (0.76 g., 1.3 mmol) in $CH_3OH$ (30 ml). The reaction mixture was refluxed for 40 minutes; the heating was interrupted and it was stirred while cooling at room temperature. The catalyst was filtered and the clear and colourless solution was evaporated to dryness. 330 mg of white solid were obtained. $[a]^{20}_D$=+8.04° (c=1% $CH_3OH$) M.p.=190° C. dec. (as hydrochloride salt, from diethyl ether); M.S. (C.I.)=454 m/e [M+H] Analysis: $C_{25}H_{32}Cl\ N_3O_5$

|  | C | H | N |
|---|---|---|---|
| Found % | 60.70 | 6.52 | 8.41 |
| Calc. % | 60.28 | 6.58 | 8.58 |

Analogously the following compound was prepared:
R(+)-Carbazole-9-carboxylic acid {1-[2-(3-ethyl-ureido)-3-hydroxy-propyl]-piperidin-4-yl} methyl ester
Compound 13
$[a]^{20}_D$=+10.27° (c=1% $CH_3H$, as hydrochloride) M.p.= 200° C. dec. (as hydrochloride salt, from diethyl ether) M.S. (C.I.)=453 m/e [M+H] Analysis: $C_{25}H_{33}Cl\ N_4O_4$

|  | C | H | N |
|---|---|---|---|
| Found % | 61.05 | 6.75 | 11.16 |
| Calc. % | 61.40 | 6.8 | 11.46 |

EXAMPLE 4

R(+)-4-Amino-5-chloro-3-methoxybenzoic acid {1-[3-hydroxy-2-(3-phenyl-ureido)-propyl]-piperidin-4-yl} methyl ester
(Compound 14)
Into a solution of S(+)-4-amino-5-chloro-2-methoxybenzoic acid {1-[3-benzyloxy-2-(3-phenyl-ureido) propyl]piperidin-4-yl} methyl ester (1.5 g., 2.5 mmol) in $CH_3OH$ (20 ml) was introduced gaseous HCl in $CH_3CH_2OH$ until an acidic pH was obtained and the resulting reaction mixture was hydrogenated at room temperature and pressure in the presente of 5% Pd/C ( g. 0.1) for 20 hours. The catalyst was filtered and the solvent was evaporated to dryness to obtain a raw product which, after chromatography (silica gel; eluent: $CH_2Cl_2/CH_3OH/NH_4OH$=93/7/0.7) gave the desired compound as a white foamy solid (0.83 g.). The corresponding hydrochloride salt may be obtained by treating a solution of the compound in diethyl ether with gaseous HCl.

$[a]^{20}_D$=+5.64° (c=1% $CH_3OH$, as hydrocloride salt) M.p.=138–140° C. dec. (as hydrochloride salt, from diethy ether) M.S. (C.I.)=492 m/e [H+H] Analysis: $C_{24}H_{32}Cl_2N_4O_5$

|  | C | H | N |
| --- | --- | --- | --- |
| Found % | 53.31 | 6.37 | 10.42 |
| Calc. % | 54.65 | 6.12 | 10.62 |

According to the above described procedure the following compounds were obtained: R(+)-4-Amino-5-chloro-2-methoxy-benzoic acid {1-[2-(3-ethyl-ureido)-3-hydroxy-propyl]-piperidin-4-yl} methyl ester.

(Compound 15)

$[a]^{20}_D$=+11.19° (c 1% $CH_3OH$, as hydrochloride salt) M.p.=60–70° C. dec. (liophilized hydrochloride salt) M.S. (C.I.)=443 m/e [M+H] Analysis: $C_{20}H_{32}Cl_2N_4O_5$

|  | C | H | N |
| --- | --- | --- | --- |
| Found % | 50.00 | 6.93 | 11.50 |
| Calc. % | 50.11 | 6.73 | 11.69 |

R(+)-5-Fluoro-1H-indol-3-carboxylic acid {1-[2-(3-phenyl-ureido)-3-hydroxy-propyl]-piperidin-4-yl} methyl ester.

(Compound 16)

$[a]^{20}$ =+6.24° (c=1% $CH_3OH$, as hydrochloride salt) M.p.=210° C. dec. (as hydrochloride salt, from diethyl ether) M.S. (C.I.)=469 m/e ([M+H] Analysis: $C_{25}H_{30}FCl\ N_4O_4$

|  | C | H | N |
| --- | --- | --- | --- |
| Found % | 59.89 | 6.28 | 10.60 |
| Calc. % | 59.46 | 5.99 | 11.09 |

R(+)-5-Fluoro-2-methoxy-1H-indol-3-carboxylic acid [1-(2-benzyloxycarbonyl-amino-3-hydroxy-propyl)-piperidin-4-yl]methyl ester.

(Compound 17)

$[a]^{20}_D$=+3.80° (c=1% $CH_3OH$, as hydrochloride salt) M.p. 120–130° C. dec. (as hydrochloride salt, from diethyl ether) M.S. (C.I.)=514 m/e [M+H] Analysis: $C_{27}H_{33}FCl\ N_3O_6$

|  | C | H | N |
| --- | --- | --- | --- |
| Found % | 59.12 | 6.10 | 7.58 |
| Calc. % | 58.96 | 6.05 | 7.64 |

S(-)-5-Fluoro-2-methoxy-1H-indol-3-carboxylic acid [1-(2-benzyloxycarbonyl-amino-3-hydroxy-propyl)-piperidin-4-yl]methyl ester.

(Compound 18)

$[a]^{20}_D$=3.95° (c 1% $CH_3OH$, as hydrochloride salt). M.p= 124–132° C. dec. (as hydrochloride salt, from diethyl ether) M.S. (C.I.)=514 m/e [M+H] Analysis: $C_{27}H_{33}FCl\ N_3O_6$

|  | C | H | N |
| --- | --- | --- | --- |
| Found % | 58.70 | 6.11 | 7.60 |
| Calc. % | 58.96 | 6.05 | 7.64 |

R(+)-5-Fluoro-2-methoxy-1H-indol-3-carboxylic acid [1-(2-ethoxycarbonyl-amino-3-hydroxy-propyl)piperidin-4-yl] methyl ester.

(Comnound 19)

$[a]^{20}_D$ +6.60° (c=1% $CH_3OH$, as hydrochloride salt). M.p.=110–120° C. dec. (as hydrochloride salt, from diethyl ether). M.S. (C.I.) 452 m/e [M+H] Analiyis: $C_{22}H_{31}FCl\ N_3O_6$

|  | C | H | N |
| --- | --- | --- | --- |
| Found % | 54.10 | 6.43 | 8.58 |
| Calc. % | 54.15 | 6.40 | 8.61 |

S(-)-5-Fluoro-2-methoxy-1H-indol-3-carboxylic acid [1-(2-ethoxycarbonyl-amino-3-hydroxy-propyl)-piperidin-4-yl]methyl ester.

(Compound 20)

$[a]^{20}_D$ =6.43° (c=1% $CH_3OH$, as hydrochloride salt) M.P. 109–114° C. dec. (as hydrochloride salt, from diethyl ether). M.S. (C.I.)=452 m/e [M+H] Analysis: $C_{22}H_{31}FCl\ N_3O_6$

|  | C | H | N |
| --- | --- | --- | --- |
| Found % | 53.99 | 6.45 | 8.55 |
| Calc. % | 54.15 | 6.40 | 8.61 |

Description 8
S(-)-1° (4-Hydroxymethyl-piperidin-1-yl)-2-benzyloxycarbonylamino-propan-1-one A solution of 4-piperidinemethanol (14.2 g., 0.123 mol) [J. Med Chem. (1991) 34, 1073] in anhydrous THF (140⁻ml) was added to a solution of CBZ-L-alanine (25 g., 0.112 mol) and 1,1-carbonyldiimidazole (18.2 g., 0.112 mol) in anhydrous THF (250 ml), cooled at 5° C. The reaction mixture, after 4 hours under stirring at room temperature, was evaporated to dryness and the residue was dissolved into ethyl acetate. The organic solution was washed with 5% aqueous solution of hydrochloric acid, with water, with 17% aqueous solution of $Na_2CO_3$ and evaporated to dryness. The residue was purified by chromatography (silica gel; eluent: $CH_2Cl_2$/$CH_3OH$=98/2) to give 24.8 g. of the desired product as a clear thick oil. $[a]^{20}_D$=-9.2 (c=1% in $CH_3OH$). Analogously the following products were prepared: R(+)-1-(4-Hydroxymethyl-piperidin-1-yl)-2-benzyloxycarbonylamino-propan-1-one $[a]^{20}_D$=+9.32° (c=1% $CH_3OH$) S(-)-1-(4-Hydroxymethyl-piperidin-1-yl)-2-t-butoxycarbonylamino-3-benzyloxy-propan-1-one $[a]^{20}_D$=-11.99° (c=1% $CH_3OH$); M.p 75° C. (dec.)

Description 9
S(-)-1-[4-(2-Nitrophenyl-amino-carbonyloxymethyl)-piperidin-1-yl]-2-benzyloxycarbonyl-amino-propan-1-one A solution of 2-nitrophenylisocyanate (9.2 g., 56.1 mmol) and S(-)-(4-hydroxymethyl-1-yl)-2-benzyloxycarbonyl-propan-1-one (18 g., 56.1 mmol) in THF (200 ml) was stirred at room temperature for 24 hours. The reaction mixture was evaporated to dryness and the desired product was obtained after chromatographic purification (silica gel; eluent: cyclohexane/ethyl acetate =50/50) as a low melting solid 17.5 g. $[a]^{20}_D$=-2.47° (c=1% $CH_3OH$). Analogously was prepared: R(+)-1-[4-(2-Nitrophenylamino-carbonyloxymethyl)-piperidin-1-yl]-2-benzyloxycarbonyl-propan-1-one [a]$^{20}_D$=+2.41 (c=1% CH$_3$OH).

Description 10

S(+)-3-[4-(2-Nitrophenyl-amino-carbonyloxymethyl)-piperidin-1-yl]-2-benzyloxycarbonyl-amino-propane A solution of S(−)-1-[4-(2-nitrophenyl-amino-carbonyloxymethyl)-piperidin-1-yl]-2-benzyloxycarbonyl-amino-propan-1-one (16.5 g., 34.1 mmol) and 1M borane complex in THF (102 ml) in tetrahydrofuran was refluxed for 4 hours. The reaction mixture was evaporated to dryness and partitioned between diethyl ether and an aqueous solution of 5% HCl. The aqueous solution was washed once more with ethyl acetate, made alkaline with aqueous solution of 17% Na$_2$CO$_3$ and the solid which precipitated was extracted into ethyl acetate. The organic solution was crystallized from, dried and evaporated to dryness. The residue was crystallized from isopropyl ether to give the desired compound (12.3 g.) [a]$^{20}_D$=9.47° (c=1% CH$_3$OH). Analogously was prepared: R(−)-3-[4-(2-Nitrophenyl-amino-carbonyloxymethyl)-piperidin-1-yl]-2-benzyloxycarbonyl-amino-propane [a]$^{20}_D$=−9.51° (c=1% CH$_3$OH).

Description 11

S(+)-3-[4-(2-Aminophenyl-amino-carbonyloxymethyl)-piperidin-1-yl]-2-benzyloxycarbonylamino-propane A solution of S(+)-3-[4-(2-nitrophenylamino-carbonyloxymethyl)-piperidin-1-yl]-2-benzyloxycarbonyl-amino-propane (10 g., 21.2 mmol) and SnCl$_2$.2H$_2$O (24 g., 106.4 mmol) in 95% EtOH was refluxed for 30 minutes, then cooled and evaporated to dryness. The residue was taken up into water with diethyl ether. The aqueous phase was washed with ethyl acetate, made alkaline with aqueous solution of 17% Na$_2$CO$_3$ and extracted into ethyl acetate. From the dried and evaporated solution the desired product was obtained as a white solid, pure enough to be used in the next step (7.7 g.). [a]$^{20}_D$=−10.41° (c=1% CH$_3$OH). Analogously was prepared: R(−)-3-[4-(2-amino-phenylamino-carbonyloxymethyl)-piperidin-1-yl]-2-benzyloxycarbonyl-amino-propane [a]$^{20}_D$=−10.32° (c=1% CH$_3$OH).

EXAMPLE 5

S(+)-2-Oxo-2,3-dihydro-benzimidazol-1-carboxylic acid [1-(2-benzyloxycarbonyl-amino)-propyl-piperidin-4-yl]-methyl ester (Compound 21)

A solution of S(−)-3-[4-(2-aminophenyl-amino-carbonyloxymethyl)-piperidin-1-yl]-2-benzyloxycarbonyl-amino-propane (6.7 g., 15.2 mmol) and diphosgene (3.6 g., 18.24 mmol) in CH$_2$Cl$_2$ (100 ml) was stirred at room temperature for 20 hours. The solution was evaporated to dryness and the residue was partitioned between ethyl acetate and a 5% HCl aqueous solution. The acid solution was treated with ethyl acetate, made alkaline with 17% Na$_2$CO$_3$ aqueous solution and extracted into CH$_2$Cl$_2$. From these solutions, dried and evaporated to dryness, the desired product as raw material was obtained. It was purified by conversion into the corresponding hydrochloride salt and next recrystallization from acetone (3.4 g.) [a]$^{20}_D$=+17.14° (c=1% CH$_3$OH). M.p. 187–188° C dec. (as hydrochloride salt) M.S. (C.I.) =467 m/e (M+H) Analysis C$_{25}$H$_{31}$Cl N$_4$O$_5$

|  | C | H | N |
|---|---|---|---|
| Found % | 59.07 | 6.21 | 10.99 |
| Calc. % | 59.70 | 6.25 | 11.14 |

Analogously was prepared: R(−)-2-Oxo-2,3-dihydro-benzimidazol-1-carboxylic acid [1-(2-benzyloxycarbonylamino)-propyl-piperidin-4-yl]-methyl ester (Compound 22)

[a]$^{20}_D$=−17.20° (c=1% CH$_3$OH). M.p. 185–188° C. dec. (as hydrochloride salt) M.S. (C.I.) =467 m/e (M+H) Analysis C$_{25}$H$_{31}$Cl N$_4$O$_5$

|  | C | H | N |
|---|---|---|---|
| Found % | 59.19 | 6.20 | 11.12 |
| Calc. % | 59.70 | 6.25 | 11.14 |

EXAMPLE 6

S(+)-3-Ethyl-2-oxo-2,3-dihydro-benzimidazol-1-carboxylic acid [1-(2-benzyloxycarbonyl-amino)-propyl-piperidin-4-yl]-methyl ester (Compound 23)

Iodoethane (1.44 g., 9.2 mmol) was added at room temperature to a solution of S(+)-2-oxo-2,3-dihydro-benzimidazol-1-carboxylic acid [1-(2-benzyloxycarbonyl-amino)-propyl-piperidin-4-yl]methyl (4.3 g., 9.2 mmol) and 80% NaH (0.28 g., 9.2 mmol) in anhydrous DMF (40 ml). The solution was stirred at room temperature for 8 hours, then it was poured into water (200 ml). The precipitate was extracted into ethyl acetate and the organic solution was extracted again with 5% HCl aqueous solution. The solution was washed more once with ethyl acetate, made alkaline with aqueous solution of 17% Na$_2$CO$_3$ and extracted again with CH$_2$Cl$_2$. From this solution, after drying and evaporation to dryness, the desired compound was obtained. It was purified by chromatography (silica gel; eluent: CH$_2$Cl$_2$/CH$_3$OH=95/5). (2 g.) [a]$^{20}_D$=+17.33° (c=1% in CH$_3$OH). M.p. 185° C. dec. (as hydrochloride salt) M.S.(C.I.) =495 m/e (M+H) Analysis C$_{27}$H$_{35}$Cl N$_4$O$_5$

|  | C | H | N |
|---|---|---|---|
| Found % | 60.59 | 6.68 | 10.45 |
| Calc. % | 61.07 | 6.64 | 10.55 |

Analogously was prepared: R(−)-3-Ethyl-2-oxo-2,3-dihydro-benzimidazol-1-carboxylic acid-[1-(2-benzyloxycarbonyl-amino)-propyl-piperidin-4-yl]-methyl ester (Compound 24)

[a]$^{20}_D$=−17.45° (c=1% CH$_3$OH). M.p. 184–187° C. dec. (as hydrochloride salt) M.S. (C.I.) =495 m/e (M+H) Analysis C$_{27}$H$_{35}$Cl N$_4$O$_5$

|  | C | H | N |
|---|---|---|---|
| Found % | 61.18 | 6.70 | 10.48 |
| Calc. % | 61.07 | 6.64 | 10.33 |

Description 12

R(+)-[1-(2-t-Butoxycarbonylamino-3-benzyloxy-propyl)-piperidin-4-yl]-methanol

A solution of S(−)-t-butoxycarbonylamino-3-benzyloxy-1-(4-hydroxymethyl-piperidin-1-yl)-propan-1-one (16.5 g., 42 mmol) and 1 M borane complex in THF (126 ml) in anhydrous THF was refluxed for 16 hours under stirring. The reaction mixture was evaporated to dryness, taken up into diethyl ether and from this solution it was extracted twice with 5% HCl aqueous solution. The solutions were collected, washed with diethyl ether and made alkaline with aqueous solution of 17% $Na_2CO_3$. The oily product, which separated, was extracted into ethyl, acetate; this solution was washed to neutral dried and evaporated to dryness. The desired product was obtained as a colourless oil, after purification of the raw material by chromatography (silica gel; eluent: $CH_2Cl_2/CH_3OH=95/5$). (11.2 g.) $[a]^{20}_D=+12.02°$ (c=1% $CH_3OH$). Analogously may be prepared: S(−)-1-(2-t-butoxycarbonylamino-3-benzyloxy-propyl)-piperidin-4-yl]-methanol. $[a]^{20}_D=−12.02°$ (C =1% $CH_3OH$)

Description 13

R(+)-5-Fluoro-1H-indol-3-carboxylic acid [1-(2-t-butoxycarbonylamino-3-benzyloxy-propyl)-piperidin-4-yl] methyl ester Trifluoroacetic anhydride (5.2 g., 24.5 mmol) was added under stirring to a suspension of 5-fluoro-1H-indol-3-carboxylic acid [J.Med. Chem. (1991), 34, 140] (4 g., 22.3 mmol) in $CH_2Cl_2$, cooled at S.C. After 90 minutes, stirring at the same temperature, methanesulfonic acid (2.2 g., 22.3 mmol) following by a solution of S(+)-[1-(2-t-butoxycarbonylamino-3-benzyloxy-propyl)-piperidin-4-yl] methanol (8.5 g., 22.32 mmol) in $CH_2Cl_2$ (5 ml) were rapidly added. The reaction mixture was stirred for 24 hours at room temperature, then evaporated to dryness. The desired product was obtained as a low melting solid after purification of the raw material by chromatography (silica gel; eluent: $CH_3OH/CH_2Cl_2$) $NH_4OH=95/5/0.5$). (1.9 g.) $[a]^{20}_D=+8.59°$ (c=1% $CH_3OH$).

Description 14

R(+)-5-Fluoro-2-methoxy-1H-indol-3-carboxylic acid [1-(2-t-butoxycarbonylamino-3-benzyloxy-propyl)-piperidin-4-yl]methyl ester A solution of S(+)-5-fluoro-1H-indol-3-carboxylic acid [1-(2-t-butoxycarbonylamino-3-benzyloxy-propyl)-piperidin-4-yl]methyl ester (0.5 g., 0.92 mmol) and N-chlorosuccinimide (0.19 g. 1.38 mmoli) in $CHCl_3$ was stirred overnight at room temperature. It was evaporated to dryness and the residue was taken up with $CH_3OH$ (20 ml) and the resulting solution was stirred for 24 hours. After evaporation to dryness, the residue was dissolved in $CH_2Cl_2$; this solution was washed once more with 17% $Na_2CO_3$ aqueous solution and then with water. After drying and evaporation to dryness, the desired product was obtained as a colourless oil after purification of the residue by chromatography (silica gel; eluent: $CH_2Cl_2$) $CH_3OH=97/3$). (0.18 g) $[a]^{20}_D=+5.70°$ (c=1% $CH_3OH$). Analogously the following products were prepared: R(+)-5-Fluoro-2-methoxy-1H-indol-3-carboxilic acid [1-(2-ethoxycarbonylamino-3-benzyloxy-propyl)-piperidin-4-yl] methyl ester. $[a]^{20}_D=+3.99°$ (c=1% $CH_3OH$) S(−)-5-Fluoro-2-methoxy-1H-indol-3-carboxylic acid [1-(2-ethoxycarbonylamino-3-benzyloxy-propyl)-piperidin-4-yl] methyl ester. $[a]^{20}_D=−4.06°$ (c=1% $CH_3OH$) S(−)-5-Fluoro-2-methoxy-1H-indol-3-carboxylic acid [1-(2-t-butoxycarbonylamino-3-benzyloxy-propyl)-piperidin-4-yl] methyl ester. $[a]^{20}_D=−5.46°$ (c=1% $CH_3OH$)

Description 15

S(−)-1-(2-t-Butoxycarbonylamino-3-benzyloxy-propionyl)-4-carbamoyl-piperidine 1,1-carbonyldiimidazole (5.5 g., 33.8 mmol) was added portionwise under stirring to a solution of N-t-Boc-O-Bz-L-serine (10 g., 33.8 mmol) in anhydrous THF (58 ml). After 30 minutes isonipecotamide (4.34 g., 33.8 mmol) was introduced and the resulting suspension was stirred overnight at room temperature, and then evaporated to dryness. The residue was taken up into ethyl acetate and the organic solution was subsequently washed with aqueous solution of 5% HCl, then with $H_2O$ and with 8% $Na_2CO_3$ aqueous solution. After drying and evaporation to dryness, the desired product was obtained as a low melting, white-spongy solid (11.9 g.). $[a]^{20}_D=−10.28°$ (c=1% $CH_3OH$). Analogously the following products may be prepared: R(+)-1-(t-Butoxycarbonylamino-3-benzyloxypropyl)-4-carbamoyl-piperidine. $[a]^{20}_D=+10.41°$ (c=1% $CH_3OH$). S(−)-1-(t-Butoxycarbonylamino-4-methylthio-butyryl)-4-carbamoyl-piperidine. $[a]^{20}_D=−24.19°$ (c=1% $CH_3OH$). M.p. 132–134° C. dec. R(+)-1-(t-Butoxycarbonylamino-4-methylthiobutyryl)-4-carbamoyl-piperidine. $[a]^{20}_D=+23.98°$ (c=1% $CH_3OH$). M.p. 130–132° C. dec. S(−)-3-t-Butoxycarbonylamino-4-(4-carbamoyl-piperidin-1-yl)-4-oxo-butyric acid methyl ester $[a]^{20}_D=−65.03°$ (c=1% $CH_3OH$). M.p. 121–123° C. dec. S(−)-3-Benzyloxycarbonylamino-4-(4-carbamoyl-piperidin-1-yl)-4-oxo-butyric acid methyl ester $[a]^{20}_D=−43.3°$ (c=1% $CH_3OH$). M.p. 160° C. dec. S(−)-1-(2-Benzyloxycarbonylamino)-propionyl- 4-carboxamide-piperidine $[a]^{20}_D=−10.96°$ (c=1% $CH_3OH$) R(+)-1-(2-Benzyloxy carbonylamino)-propionyl-4-carboxamide-piperidine $[a]^{20}_D=+11.05°$ (c=1% $CH_3OH$) S(−)-4-carboxamide-1-(3-phenyl-2-t-butoxycarbonylamino)-propionyl-piperidine $[a]^{20}_D=−1.2°$ (c=1% $CH_3OH$) R(+)-4-carboxamide-1-(3-phenyl-2-t-butoxycarbonylamino)-propionyl-piperidine $[a]^{20}_D=+1.35°$ (c=1% $CH_3OH$)

Description 16

R(+)-1-Benzyloxymethyl-2-(4-aminomethyl-piperidin-1-yl)-N-t-butoxycarbonyl-ethylamine)

A solution of 1 M borane complex in tetrahydrofuran (148 ml) was added portionwise in 3 hours to a solution of S(−)-1-(2-t-butoxycarbonylamino-3-benzyloxypropionyl)-4-carbamoyl-piperidine (15 g., 37 mmol) in anhydrous THF (100 ml) under refluxing. After cooling and evaporation to dryness, the residue was dissolved into ethyl acetate. It was extracted with citric acid aqueous solution, washed with ethyl acetate, make alkaline with diluted 8% $Na_2CO_3$ aqueous solution and extracted with ethyl acetate. The organic solution after anhydrification and evaporation, gave a residue from which the desired product as was obtained a clear-thick oil after chromatography (silica gel; eluent: $CH_2Cl_2/CH_3OH/NH_4OH=90/10/1$ (5.6 g.). $[a]^{20}_D=+7.21°$ (c=1% $CH_3OH$). Analogously the following products were obtained: S(−)-1-Benzyloxymethyl-2-(4-aminomethyl-piperidin-1-yl)-N-t-butoxycarbonyl ethylamine. $[a]^{20}_D=−8.01°$ (c=1% $CH_3OH$). R(+)-1-(4-Aminomethyl-piperidin-1-yl-methyl)-3-methyl-thio-N-t-butoxycarbonyl-propylamine. $[a]20_D=+14.48°$ (c=1% $CH_3OH$) S(−)-1° (4-, kminomethyl-piperidin-1-yl-methyl)-3-methyl-thio-N-t-butoxycarbonyl-propylamine. $[a]^{20}_D=−14.61°$ (c=1% $CH_3OH$) S(−)-3-Benzyloxycarbonylamino-4-(4-aminomethyl-piperidin-1-yl)-butyric acid methyl ester. $[a]^{20}_D=−1.90$ (c=1% $CH_3OH$). S(+)-2-(4-Aminomethyl-piperidin-1-yl)-benzyloxycarbonylamino-1-methyl-ethylamine $[a]^{20}_D=+9.05°$ (c=1% $CH_3OH$) R(−)-2-(4-Aminomethyl-piperidin-1-yl)-benxyloxecarbonyl-amino-1-methyl-ethylamine $[a]^{20}_D=−9.28°$ (c=1% $CH_3OH$) S(+)-4-aminomethyl-1-[(3-phenyl-2-t-butoxycarbonyl-amino)-porpyl]piperidine $[a]^{20}_D=+1.43$ (c=1% $CH_3OH$) R(−)-4-amiminomethyl-(3-phenyl-2-t-butoxycarbonylamino)-propyl]-piperidine $[a]^{20}_D=−1.53°$ (c=1% $CH_3OH$)

Description 17

3Ethyl-2-oxo-2,3-dihydro-benzimidazol-1-chlorocarbonyl.

A solution of 1-ethyla2-oxo-2,3-dihydro-benzimidazole (5 g., 0.025 ml) and diphosgene (5.6 g., 3.5 ml) in THF was heated at 60° C. in the presence of a small amount of activated carbone under stirring. The solution was kept under stirring at the temperature of 60° C. for 5hours. After filtration and cooling, it was evaporated to dryness obtaining a residue from which, after crystallization with diethyl ether, the desired product was obtained as a white solid (4.4 g.). M.p. 99–105° C. dec. Analogously was prepared: 3-Isopropyl-2-oxo-2,3-dihydro-benzimidazol-1-chlorocarbonyl M.p. 110–112° C. dec.

Description 18

R(+)-3-Ethyl-2-oxo-2,3-dihydro-benzimidazol-1-carboxamide-[1-(2-t-butoxycarbonylamino-3-benzyloxy-propyl)-piperidin-4-yl-methyl]

3-Ethyl-2-oxo-2,3-dihydro-benzimidazol-1-chlorocarbonyl (2.14 g., 10.8 mmol) was added portionwise, under stirring, to a solution of S(−)-1-benzyloxymethyl-2-(4-aminomethyl-piperidin-1-yl)-N-t-butoxycarbonylethylamine (3.4 g., 9 mmol) in $CH_2Cl_2$ (50 ml). After 4 hours under stirring at room temperature the reaction mixture was evaporated to dryness. The residue was dissolved in ethyl acetate, then washed once more with diluted 8% $Na_2CO_3$ aqueous solution. After anhydrification and evaporation to dryness, the desired product was purified by chromatography (silica gel; eluent: cyclohexane/ethylacetate 1/1) (3.6 g.); grey solid $[a]^{20}_D$=5.19° (c=1% $CH_3OH$). Analogously the following compounds were prepared: R(+)-3-Ethyl-2-oxo-2,3-dihydro-benzimidazol-1-carboxamide-[1-(2-t-butoxycarbonylamino-4-methylthio-butyl)-piperidin-4-yl-metil]. $[a]^{20}_D$=+9.95° (c=1% $CH_3OH$) S(−)-3-Ethyl-2-oxo-2,3-dihydro-benzimidazol-1-carboxamide-[1-(2-t-butoxycarbonylamino-4-methylthio-butyl)-piperidin-4-yl-methyl]. $[a]^{20}_D$=+10.01° (c=1% $CH_3OH$) S(−)-2-Oxo-2,3-dihydro-benzimidazol-1-carboxamide-[1-(2-t-butoxycarbonylamino-4-methylthio-butyl)-piperidin-4-yl-methyl]. $[a]^{20}_D$=−10.06° (c=1% $CH_3OH$). M.p. 65–68° C. R(−)-3-Ethyl-2-oxo-2,3-dihydro-benzimidazol-1-carboxamide-[1-(2-t-butoxycarbonylamino-3-benzyloxy-propyl]-piperidin-4-yl-methyl. $[a]^{20}_D$=−4.38° (c=1% $CH_3OH$) S(−)-3-Isopropyl-2-oxo-2,3-dihydro-benzimidazol-1-carboxamide[1-(2-t-butoxycarbonylamino-4-methylthiobutyl)-piperidin-4-yl-methyl]. $[a]^{20}_D$=−9.91° (c=1% $CH_3OH$). M.p. 55° C. dec. S(+)-3-Ethyl-2-oxo-2,3-dihydro-benzoimidazole-1-carboxamide-N-{1[(2-t-butoxycarbonyl-amino-3-phenyl)-propyl]-piperidin-4-yl-methyl} $[a]^{20}_D$=+1.63° R(−)-3-Ethyl-2-oxo-2,3-dihydro-benzomidazole-1-carboxamide-N-{1-[(2-t-butoxycarbonylamino-3-phenyl)-propyl]-piperidin-4-yl-methyl} $[a]^{20}_D$=−1.70°

Description 19

S(+)-3-Benzyloxycarbonylamino-4-(4-aminomethyl-piperidin-1-yl)-butyrramide

Gaseous anhydrous $NH_3$ was slowly bubbled for 8 hours into a solution of S(−)-3-benzyloxycarbonylamino-4-(4-aminomethyl-piperidin-1-yl)-butiric acid methyl ester (0.7 g., 1.9 mmol) in $CH_3OH$ (20 ml). The solution was kept, under stirring, for two days at room temperature, and then evaporated to dryness. The desired product was obtained after chromatographic purification of the residue (silica gel, eluent: $CH_2Cl_2/CH_3OH/NH_4OH$=80/20/2). (320 mg.). Light-brown solid. $[a]^{20}_D$=+3.89° (c=1% $CH_3OH$)

EXAMPLE 7

S(+)-3-Ethyl-2-oxo-2,3-dihydro-benzimidazol-1-carboxamide-[1-(2-benzyloxycarbonylamino-3-carbamoyl-propyl)-piridin-4-yl-methyl]

(Compound 25)

A solution of S(+)-3-benzyloxycarbonylamino-4-(4-aminomethyl-piperidin-1-yl)-butyramide (0.19 g., 0.54 mmol) and 3-ethyl-2-oxo-2,3-dihydro-benzimidazol-1-chlorocarbonyl (0.13 g., 0.65 mmol) in $CH_2Cl_2$ (20 ml) was stirred at room temperature for 4 hours in the presence of triethylamine (0.083 g., 0.70 mmol). The reaction mixture was extracted with a diluted 5% HCl aqueous solution; the acid solution, after further washing with ethyl acetate, was neutralized with aqueous diluted 8% $Na_2CO_3$ solution. The oily product, which separated, was extracted into ethyl acetate; from this solution after washing with water, anhydrification and evaporation to dryness, the raw desired product was obtained. This was purified by chromatography (silica gel, eluent: $CH_2Cl_2/CH_3OH/NH_4OH$=95/5/0.5). (0.15 g.) $[a]^{20}_D$=+3.21° (c=1% in CH OH). M.p. 120° C. dec. (from diethyl ether) M.S. (C.I.)=537 m/e (M+H) Analysis $C_{28}H_{36}N_6O_5$

|  | C | H | N |
|---|---|---|---|
| Found % | 61.98 | 6.79 | 15.60 |
| Calc. % | 62.67 | 6.76 | 15.67 |

R(−)-3-Ethyl-2-oxo-2,3-dihydro-benzimidazol-1-carboxamide-N-{1-[(2-benzyloxy-carbonylamino)-propyl]-piperidin-4-yl-methyl}

(Compound 42)

$[a]^{20}_D$=−18.41° (c=1% in $CH_3OH$). M.p. 177–178° C. dec. (as hydrocloride salt) M.S. (C.I.)=494 m/e (M+H) Analysis $C_{27}H_{36}$ Cl $N_5O_4$

|  | C | H | N |
|---|---|---|---|
| Found % | 60.53 | 6.83 | 13.02 |
| Calc. % | 61.18 | 6.85 | 13.21 |

S(+)-3-Ethyl-2-oxo-2,3-dihydro-benzimidazol-1-carboxamide-N-{1-[(2-benzyloxy-carbonylamino)-propyl]-piperidin-4-yl-methyl}

(Compound 43)

$[a]^{20}_D$=+17.97° (=1% in $CH_3OH$). M.p. 178–180° C. dec. (as hydrocloride salt) M.S. (C.I.)=494 m/e (M+H) Analysis $C_{27}H_{36}$ Cl $N_5O_4$

|  | C | H | N |
|---|---|---|---|
| Found % | 60.85 | 6.81 | 13.04 |
| Calc. % | 61.18 | 6.85 | 13.21 |

R(−)-3-Ethyl-2-oxo-2,3-dihydro-benzimidazol-1-carboxamide-N-{1-[(2-benzyloxy-carbonylamino)-3-phenyl-propyl]-piperidin-4-yl-methyl}

(Compound 44)

$[a]^{20}$=−3.35° (c=1% in $CH_3OH$ 80—$CH\ Cl_3$ 20). M.p. 136–138° C. dec. M.S. (C.I.)=570 m/e (M+H) Analysis $C_{33}H_{39}N_5O_4$

|         | C     | H    | N     |
|---------|-------|------|-------|
| Found % | 69.26 | 6.94 | 12.16 |
| Calc. % | 69.57 | 6.90 | 12.29 |

S(+)-3-Ethyl-2-oxo-2,3-dihydro-benzimidazol-1-carboxamide-N-{1-[2-benzyloxy-carbonylamino)-3-phenyl-propyl]-piperidin-4-yl-methyl}
(Compound 45)
$[a]^{20}_D$=+3.24° (c=1% in CH$_3$OH 80-CH Cl$_3$ 20). M.p. 136–138° C. dec. M.S. (C.I.)=570 m/e (M+H) Analysis C$_{33}$H$_{39}$ N$_5$O$_4$

|         | C     | H    | N     |
|---------|-------|------|-------|
| Found % | 69.02 | 6.88 | 12.15 |
| Calc. % | 69.57 | 6.90 | 12.29 |

S(−)-3-Ethyl-2-oxo-2,3-dihydro-benzoimidazole-1-carboxamide-N-{1-[(2-ethoxy-carbonylamino-3-carbamoyl)-propyl]-piperidin-4-yl-methyl}
(Compound 31)
$[a]^{20}_D$=−1.1° (c=1% in CH$_3$OH). M.p. 128–130° C. dec. M.S. (C.I.)=475 m/e (M+H) Analysis C$_{29}$H$_{34}$ N$_6$O$_5$

|         | C     | H    | N     |
|---------|-------|------|-------|
| Found % | 57.90 | 7.18 | 17.58 |
| Calc. % | 58.21 | 7.22 | 17.71 |

Description 20
R(+)-3-Ethyl-2-oxo-2,3-dihydro-benzimidazol-1-carboxamide-[1-(2 amino-3-benzyloxypropyl)-piperidin-4-yl-methyl].

Dry gaseous HCl was bubbled for 20 minutes into solution of S(+)-3-ethyl-2-oxo-2,3-dihydro-benzimidazol-1-carboxamide-[1-(2-t-butoxycarbonylamino-3-benzyloxypropyl)-piperidin-4-yl-methyl] (2.5 g., 4.41 mmol) in ethyl acetate (25 ml), cooled at 5° C. It was evaporated to dryness and the obtained residue, after crystallization with diethyl ether, gave the desired product as dihydrochloride salt. $[a]^{20}_D$=+1.97° (c=1% in CH$_3$CH). M.p. 85–90° C. dec. Analogously the following products were prepared: S(+)-3-Ethyl-2-oxo-2,3-dihydro-benzimidazol-1-carboxamide[1-(2-amino-4-methythio-butyl)-piperidin-4-yl-methyl]. $[a]^{20}_D$=+12.88° (c=1% CH$_3$OH, as hydrochloride, salt). M.p. 118–120° C. dec. (as hydrochloride salt) R(−)-3-Ethyl-2-oxo-2,3-dihydro-benzimidazol-1-carboxamide-[1-(2-amino-4-methylthio-butyl)-piperidin-4-yl-methyl. $[a]^{20}_D$=−12.52° (c=1% CH$_3$OH, as hydrochloride salt). M.p. 112–115° C. dec. (as hydrochoride salt) S(+)-3-Isopropyl-2-oxo-2,3-dihydro-benzimidazol-1-carboxamide-[1-(2-amino-4-methylthio-butyl)-piperidin-4-yl-methyl]. $[a]^{20}_D$=+14.19° (c 1% CH$_3$OH, as hydrochloride salt). M.p. 160–165° C. dec. (as hydrochloride salt) S(+)-2-Oxo-2,3-dihydro-benzimidazol-1-carboxamide-[1-(2-amino-4-methylthio-butyl)-piperidin-4-yl-methyl]. $[a]^{20}_D$=+15.61° (c=1% in CH$_3$OH, as hydrochloride salt). M.p. 220–225° C. dec. (as hydrochloride salt) S(+)-3-Ethyl-2-oxo-2,3-dihydro-benzoimidazole-1-carboxamide-N-{1-[(2-amino-3-phenyl)-propyl]-piperidin-4-yl-methyl} $[a]^{20}_D$=+6.12° R(−)-3-Ethyl-2-oxo-2,3-dihydro-benzoimidazole-1-carboxamide-N-{1-[(2-amino-3-phenyl)-propyl]-piperidin-4-yl-methyl} $[a]^{20}_D$=−6.01°

EXAMPLE 8

S(−)-3-Ethyl-2-oxo-2,3-dihydro-benzimidazol-1-carboxamide-{1-[2-(3-phenyl-ureido)-4-methylthio-butyl]-piperidin-4-yl-methyl}
(Compound 26)

A solution of S(+)-3-ethyl-2-oxo-2,3-dihydrobenzimidazol-1-carboxamide-[1(2-amino-4-methylthio-butyl)-piperidin-4-yl-methyl) (0.8 g., 1.90 mmol) and phenylisocyanate (0.227 g., 1.9 mmol) in THF (15 ml) was stirred at room temperature for 30 minutes, then evaporated to dryness. The desired product was obtained in a form after purification by chromatography (silica gel, eluent: CH$_2$Cl$_2$/CH$_3$OH=95/5). (0.65 g.). $[a]^{20}_D$=−5.80° (c=1% CH$_3$OH) M.p. 195–198° C. dec. (as hydrochloride salt). M.S. (C.I.)=539 (m/e (M+H) Analysis C$_{28}$H$_{39}$Cl N$_6$O$_5$S

|         | C     | H    | N     |
|---------|-------|------|-------|
| Found % | 59.00 | 6.80 | 14.66 |
| Calc. % | 58.47 | 6.83 | 14.61 |

Analogously the following products may be prepared: R(+)-3-Ethyl-2-oxo-2,3-dihydro-benzimidazol-1-carboxamide{1-[2-(3-phenyl-ureido)-4-methylthio-butyl]-piperidin-4-yl-methyl}
(Compound 27)
$[a]^{20}_D$=−5.49° (c=1% CH$_3$OH). M.p. 195–200° C. dec. (as hydrochloride salt) M.S. (C.I.)=+539 m/e (M+H) Analysis C$_{28}$H$_{39}$Cl N$_6$O$_3$S

|         | C     | H    | N     |
|---------|-------|------|-------|
| Found % | 58.20 | 6.90 | 14.50 |
| Calc. % | 58.47 | 6.83 | 14.61 |

S(+)-3-Ethyl-2-oxo-2,3-dihydro-benzimidazol-1-carboxamide-{1-[2-(3-ethyl-ureido)-4-methylthio-butyl]-piperidin-4-yl-methyl}
(Compnound 28)
$[a]^{20}_D$=+3.85° (c=1% CH$_3$OH, as hydrochloride salt). M.p. 189–194° C. dec. (as hydrochloride salt) M.S. (C.I.)= 491 m/e (M+H) Analysis C$_{24}$H$_{39}$Cl N$_6$O$_3$S

|         | C     | H    | N     |
|---------|-------|------|-------|
| Found % | 54.60 | 7.53 | 15.66 |
| Calc. % | 54.69 | 7.46 | 15.94 |

S(−)-2-oxo-2,3-dihydro-benzimidazol-1-carboxamide-{1-[2-(3-phenyl-ureido)-4-methylthio-butyl]-piperidin-4-yl-methyl}
(Compound 29)
$[a]^{20}_D$=−5.08° (c=1% CH$_3$OH). M.p. 174–176° C. dec. M.S. (C.I.)=511 m/e (H+H) Analysis C$_{26}$H$_{34}$N$_6$O$_3$S

|         | C     | H    | N     |
|---------|-------|------|-------|
| Found % | 61.02 | 6.80 | 16.38 |
| Calc. % | 61.15 | 6.71 | 16.46 |

R(+)-3-Ethyl-2-oxo-2,3-dihydro-benzimidazol-1-carboxamide-{1-[3-benzyloxy-2-(3-phenyl-ureido)-propyl]-piperidin-4-yl-methyl}. $[a]D$=+7.6° (c=1% CH$_3$OH, as hydrochloride salt). M.p. 170–180° C. dec. (as hydrochloride salt) R(+)-3-Ethyl-2-oxo-2,3-dihydro-benzimidazol-1-carboxamide-{1-[3-benzyloxy-2-(3-ethyl-ureido)-propyl]-piperidin-4-yl-methyl}. $[a]^{20}{}_D$=+8.69° (c=1% $CH_3OH$) S(+)-3-Ethyl-2-oxo-2,3-dihydro-benzimidazol-1-carboxamide-{1-[2-(3-phenyl-ureido)-3-carbamoyl-propyl]-piperidin-4-yl-methyl}

(Compournd 30)

$[a]^{20}{}_D$=+0.65° (c=1% $CH_3OH$, as hydrochloride salt). M.p. 126–130° C. dec. (as hydrochloride salt) M.S. (C.I.)= 522 m/e (M+H) Analysis $C_{27}H_{35}N_7O_4$

|  | C | H | N |
|---|---|---|---|
| Found % | 62.03 | 6.80 | 18.71 |
| Calc. % | 62.17 | 6.76 | 18.80 |

EXAMPLE 9

S(+)-2-Oxo-2,3-dihydro-benzimidazol-1-carboxamide-[1-(2-ethoxycarbonylamino-4-methylthio-butyl)-piperidin-4-yl-methyl]

(Compound 32)

Ethylchloroformate (0.2 g., 1.83 mmol) was added under stirring to a suspension of S(+)-2-oxo-2,3-dihydro-benzimidazol-1-carboxamide-1-[(2-amino-4-methylthio-buthyl)-piperidin-4-yl-methyl] (80.6 g., 1.53 mmol) in $CH_2Cl_2$ (10 ml). The reaction mixture was kept overnight, then evaporated to dryness. The residue was taken up into $H_2O$ (10 ml) and into an aqueous 17% HCl solution (0.5 ml). The obtained precipitate was filtered and dried. After recrystallization from acetone the desired product was obtained as hydrochloride salt. 0.53 g. $[a]^{20}{}_D$=+4.98 (c=1% $CH_3OH$, as hydrochloride salt). M.p. 240° C. dec. (as hydrochloride salt) M.S. (C.I.)=464 m/e (M+H) Analysis $C_{22}H_{34}Cl N_5O_4S$

|  | C | H | N |
|---|---|---|---|
| Found % | 52.70 | 6.91 | 13.90 |
| Calc. % | 52.84 | 6.85 | 14.01 |

Analogously the following products were prepared: S(+)-3-Isopropyl-2-oxo-2,3-dihydro-benzimidazol-1-carboxamide-[1-(2-ethoxycarbonylamino-4-methylthio-butyl)-piperidin-4-yl-methyl]

(Compound 33)

$[a]^{20}{}_D$=+4.72° (c=1% $CH_3OH$, as hydrochloride salt). M.p. 172–1754 C. dec. (as hydrochloride salt, from. acetone-diethyl ether) M.S. (C.I.)=506 m/e (M+H) Analysis $C_{26}H_{40}Cl N_5O_4S$

|  | C | H | N |
|---|---|---|---|
| Found % | 55.21 | 7.51 | 12.85 |
| Calc. % | 55.39 | 7.44 | 12.92 |

S(+)-3-Ethyl-2-oxo-2,3-dihydro-benzimidazol-1-carboxamide-[1-(2-ethoxycarbonylamino-4-methylthio-butyl)-piperidin-4-yl-methl]

(Compound 34)

$[a]^{20}{}_D$=+6.60° (c 1% $CH_3OH$, hydrochloride salt). M.p. 180–185° C. dec. (as hydrochloride salt from diethyl ether) M.S. (C.I.)=492 mle (M+H) Analysis $C_{24}H_{38}Cl N_5O_4S$

|  | C | H | N |
|---|---|---|---|
| Found % | 54.08 | 7.30 | 13.20 |
| Calc. % | 54.58 | 7.25 | 13.26 |

Description 21

S(−)-3-Ethyl-2-oxo-2,3-dihydro-benzimidazol-1-carboxamide-[1-(2-amino-3-hydroxy-propyl)-piperidin-4-yl-methyl]

A suspension of R(−)-3-ethyl-2-oxo-2,3-dihydro-benzimidazol-1-carboxamide-[1-(2-butoxycarbonylamino-3-benzyloxypropyl)-piperidin-4-yl-methyl] (1.5 g. 2.65 mmol) and 10% Pd/C (150 mg) in $CH_3CH_2OH$ (20 ml) was kept under shaking in the presence of a 25% solution of HCl in $CH_3CH_2OH$ (1.5 ml) in $H_2$ atmosphere at room pressure. After 48 hours, the catalyst was filtered and the solution was evaporated to dryness; the residue was dissolved in $H_2O$ and neutralized with a diluted aqueous solution of 8% $K CO_3$. The semisolid precipitate was extracted into ethyl acetate from which, after evaporation to dryness, the desired product as white and low melting solid was obtained. $[a]^{20}{}_D$=−3.3° (c=1% $CH_3OH$). Analogously was obtained: R(+)-3-Ethyl-2-oxo-2,3-dihydro-benzimidazol-1-carboxamide-[1-(2-amino-3-hydroxy-propyl)-piperidin-4-yl-methyl]. $[a]^{20}{}_D$=+3.5 (c=1% $CH_3OH$

EXAMPLE 10

R(+)-3-Ethyl-2-oxo-2,3-dihydro-benzimidazol-1-carboxamide-{1-[2-(3-phenyl-ureido)-3-hydroxy-propyl]-piperidin-4-yl-methyl}

(Compound35)

A suspension of S(+)-3-ethyl-2-oxo-2,3-dihydro-benzimidazol-1-carboxamide-(1-[3-benzyloxy-2-(3-phenyl-ureido)-propyl]-piperidin-4-yl-methyl) (0.53 g., 0.85 mmol) and 10% Pd/C (100 mg) in absolute $CH_3CH_2OH$ (10 ml) was shaken under $H_2$ atmosphere at room temperature and pressure for 48 hours. The catalyst was filtered and the solution was evaporated to dryness. The desired product was obtained as ivory solid after crystallization with diethyl ether. 0.36 g. $[a]^{20}{}_D$=+5.30° (c=1% $CH_3OH$). M.p. 98–101° C. M.S.=495 m/e (M+H) Analysis $C_{26}H_{34}N_6O_4$

|  | C | H | N |
|---|---|---|---|
| Found % | 63.05 | 7.00 | 16.87 |
| Calc. % | 63.14 | 6.93 | 16.99 |

Analogously the following compounds may be obtained: R(+)-3-Ethyl-2-oxo-2,3-dihydro-benzimidazol-1-carboxamide-{1-[2-(3-ethylureido-3-hydroxy-propyl]-piperidin-4-yl-methyl}

(Compound 36)

$[a]^{20}{}_D$=+20.50° (c=1% $CH_3OH$ as hydrochloride salt). M.p. 170–175° C. dec. (as-hydrochloride salt) M.S.=447 m/e (M+H) Analysis $C_{22}H_{35}Cl N_6O$

|  | C | H | N |
|---|---|---|---|
| Found % | 54.61 | 7.39 | 17.22 |
| Calc. % | 54.71 | 7.30 | 17.40 |

R(+)-3-Ethyl-2-oxo-2,3-dihydro-benzimidazol-1-carboxamide-[1-(2-benzyloxycarbonylamino-3-hydroxy-propyl)-piperidin-4-yl-methyl]

(Compound 37)

[a]$^{20}_D$=+15.7° (c=1% CH$_3$OH, as hydrochloride salt). M.p. 192–198° C. dec. (as hydrochloride salt, from diethyl ether) M.S.=510 m/e (M+H) Analysis C$_{27}$H$_{36}$Cl N$_5$O$_5$

|  | C | H | N |
| --- | --- | --- | --- |
| Found % | 59.17 | 6.70 | 11.99 |
| Calc. % | 59.39 | 6.65 | 12.03 |

S(−)-3-Ethyl-2-oxo-2,3-dihydro-benzimidazol-1-carboxamide[-1-1° (2-benzyloxycarbonylamino-3-hydroxy-propyl)-piperidin-4-yl-methyl]
(Compound 38)

[a]$^{20}_D$=−15.9° (c=1% CH$_3$CH, as hydrochloride salt). M.p. 194–197° C. dec. (as hydrochloride salt, from diethyl ether) M.S. (C.I.)=510 m/e (M+H) Analysis C$_{27}$H$_{36}$Cl N$_5$O$_5$

|  | C | H | N |
| --- | --- | --- | --- |
| Found % | 59.20 | 6.70 | 12.00 |
| Calc. % | 59.39 | 6.65 | 12.03 |

Description 22
S(+)-1-(2-Amino-3-phenyl-propionyl)-piperidin-4-yl-carboxamide

A solution of S(+)-1-(2-benzyloxycarbonylamino-3-phenyl-propionyl)-piperidin-4-yl-carboxamide (12.5 g., 0.03 mol) in CH$_3$OH (200 ml) was hydrogenated at room temperature and pressure in the presence of 10% Pd/C (1.2 g.) and of gaseous HCl in Et$_2$0 (3.4 ml, 0.03 mol) for 20 hours. The obtained solution, after filtration of catalyst, was evaporated to dryness to give the desired product as hydrochloride salt which was crystallized from Et$_2$O (9 g.). [a]$^{20}_D$=+33.83° (c 1% CH$_3$OH).

Description 23
S(+)-1-(2-Ethoxycarbonylamino-3-phenyl-propionyl)-piperidin-4-yl-carboxamide Ethyl chloroformate (2.67 ml, 0.027 mol) was dropped into solution of S(+)-1-(2-amino-3-phenyl-propionyl)-piperidin-4-yl-carboxamide (7 g., 0.025 mol) and triethylamine (3.5 ml, 0.025 mol) in CH$_2$Cl$_2$ (70 ml), cooled at 0° C. The reaction mixture was kept under stirring a 0° C. for 30 minutes; the solvent was evaporated to dryness, the residue was taken up with 5% HCl and extracted with ethyl acetate. The organic phase was dried and evaporated to give the desired product as white-foamy solid (5.3 g.) [a]$^{20}_D$=+8.89° (c=1% CH$_3$OH)

Description 24
S-2-(4-Ethoxycarbonylaminomethyl-piperidin-1-yl)-1-benzyethylamine S(+)-1-(2-ethoxycarboxylamino-3-phenyl-propyl)-piperidin-4-yl-carboxamide (5g.,0.015 mol) in THF (60 ml) was dropped to a solution of borane complex in THF (57.5 ml, 0.058 mol). The reaction mixture was heated at 60° C. for 6 hours; CH$_3$OH (10 ml) was added and the solvent was evaporated to dryness. The residue was taken up with an aqueous 5% HCl solution, made alkaline with aqueous 5% NaHCO$_3$ solution and extracted with CH$_2$Cl$_2$. The collected organic phases were dried and evaporated to dryness. From the residue, after purification by chromatography (silica gel; eluent: CH$_2$Cl$_2$/CH$_3$OH/NH$_4$OH=90/10/1) the desired product, sufficiently pure to be used in the next step (1.73 g.), was obtained as a yellow solid.

EXAMPLE 11

S(+)-4-amino-N-l1-[(2-etossicarbonilamino-3-phenyl-propyl)-piperidin-4-yl-methyl]-5-chloro-2-methoxy-benzamide
(Compound 39)

1,1,-Carbonyldiimidazole (0.81 g., 5 mmoli) was added to a mixture of 4-amino-5-chloro-2-methoxy-benzoic acid (1.01 g., 5 mmol) in THF (20 ml) and it was stirred for 30 minutes at room temperature. S-2-(4-ethoxycarbonylaminomethyl-piperidin-1-yl)-1-benzyl-ethylamine (1.6 g., 5 mmol) in THF (10 ml) was then dropped and stirred overnight at room temperature. The solvent was evaporated to dryness, the residue was taken up with water and extracted with ethyl acetate. The collected organic phases were dried and evaporated to dryness. From the residue, after purification by chromatography (silica gel; eluent: CH$_2$Cl$_2$/CH$_3$OH=96/4) the desired product, as a white-foamy solid was obtained (0.52 g.). The corresponding hydrochloride salt was obtained introducing dry gaseous HCl in a solution of the base in diethyl ether. [a]$^{20}_D$=+12.78° (c=1% CH$_3$OH, as hydrochloride salt). M.p. 167–169° C. dec (as hydrochloride salt, from diethyl ether) M.S.=504.05 m/e (M+H) Analysis C$_2$ H$_{36}$Cl$_2$ N$_4$O$_4$

|  | C | H | N |
| --- | --- | --- | --- |
| Found % | 56.55 | 6.79 | 10.29 |
| Calc. % | 57.88 | 6.73 | 10.39 |

The following examples describe the incorporation of the active ingredient of formula I into the conventional pharmaceutical compositions for use according to the present invention and should not be intended as limiting the invention thereto.

EXAMPLE 12

| Tablets | |
| --- | --- |
| Active ingredient of Formula I | 5 mg |
| lactose | 158 mg |
| microcrystalline cellulose | 35 mg |
| magnesium stearate BP | 2 mg |
| tablet weight | 200 mg |

Method of preparation: the active ingredient was passed through a 24 mesh sieve, blended with the lactose, microcrystalline cellulose and magnesium stearate. The resulting mixture was pressed into tables weight 200. mg each. Each tablet contains 5 g of active ingredient.

EXAMPLE 13

| Capsules | |
| --- | --- |
| Active ingredient of Formula I | 5 mg |
| lactose | 193 mg |
| magnesium stearate BP | 2 mg |
| Fill weight | 200 mg |

Method of preparation: the active ingredient was sieved and blended with the excipients. The mixture was flled into hard gelatin capsules using suitable machinery.

EXAMPLE 14

| Syrup | |
|---|---|
| Active ingredient of Formula I | 5 mg |
| hydroxypropylmethylcellulose USF | 45 mg |
| Buffer | |
| Flavour | |
| Colour | as required |
| Preservatives | |
| Sweetener | |
| Purified water BP | to 10 ml |

Method of preparation: the hydroxypropylmethylcellulose was dispersed in hot water, cooled and then mixed with an aqueous solution containing the active ingredient and the other components of the formulation. The resulting solution was adjusted to volume and mixed. The syrup was clarified by filtration.

EXAMPLE 15

| Ampoules | % w/v |
|---|---|
| Active ingredient of Formula I | 1 |
| sodium chloride BP | as required |
| water for injection BP to | 100 |

Sodium chloride may be added to adjust the tonicity of the solution and the pH may be adjusted, using acid or alkali, to that of optimum stability and/or facilitate solution of the active ingredient. Alternatively suitable buffer salts may be used. Method of preparation: the solution was prepared, clarified and filled into appropriate size ampoules sealed by fusion of the glass. The injection was sterilised by heating in an autoclave using one of the acceptable cycles. Alternatively the solution may be sterilised by filtration and filled into sterile ampoules under aseptic conditions. The solution may be packed under an inert atmosphere of nitrogen or other suitable gas.

EXAMPLE 16

| Suppositories | |
|---|---|
| Active ingredient of formula I | 15 mg |
| semisynthetic gliverides of fatty acid | 193 mg |

Method of preparation: a suspension of the active ingredient was prepared in the molten semisynthetic gliverides of fatty acids and filled, using suitable machinery, into suppository moulds.

We claim:

1. A compound of formula (I)

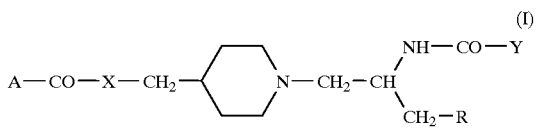

wherein

A is a group selected from substituted phenyl of structure

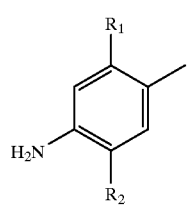

(a)

in which $R_1$ is $C_{1-3}$ alkoxy and $R_2$ is halogen; or bi- or tricyclic heterocycle selected from

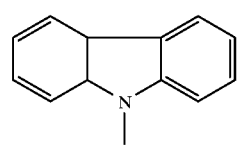

(b)

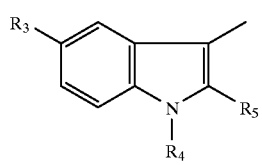

(c)

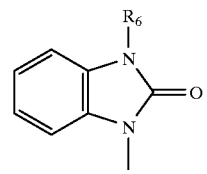

(d)

in which $R_3$ is hydrogen or halogen, $R_4$ is hydrogen or $C_{1-3}$ alkyl, $R_5$ is hydrogen or $C_{1-3}$ alkoxy, $R_6$ is hydrogen or a linear or branched $C_{1-6}$ alkyl;

X is oxygen or NH;

Y is a group of formula $-OR_7$ or $NHR_7$, wherein $R_7$ is $C_{1-3}$ alkyl, aryl or aralkyl;

R is hydrogen, phenyl, hydroxy, benzyloxy, methylthiomethyl, 3-indolyl, methoxycarbonyl or carbamoyl;

or an acid addition salt thereof with physiologically acceptable acids.

2. The compound according to claim 1, wherein A is the group (c) or (d), $R_3$ is halogen, $R_4$ is hydrogen or $C_{1-3}$ alkyl, $R_5$ is $C_{1-3}$ alkoxy, $R_6$ is linear or branched $C_{1-6}$ alkyl, X is oxygen or NH, Y is $OR_7$ wherein $R_7$ is $C_{1-3}$ alkyl, aryl or aralkyl, R is hydrogen, hydroxy, benzyloxy or carbamoyl, or an acid addition salt thereof with physiologically acceptable acids.

3. The compound according to claim 1 which is a physiologically acceptable acid salt.

4. The compound according to claim 3, wherein the physiologically acceptable acid salt is made from hydrochloric, hydrobromic, maleic, fumaric or methanesulphonic acid.

5. A process for the preparation of compounds of formula I'

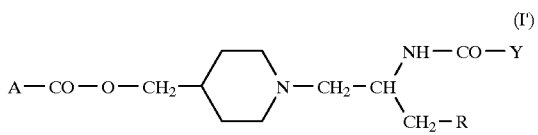

wherein
A is a group selected from
substituted phenyl of structure

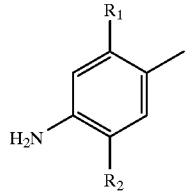

in which $R_1$ is $C_{1-3}$ alkoxy and $R_2$ is halogen; or bi- or tricyclic heterocycle selected from

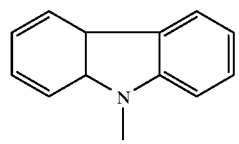

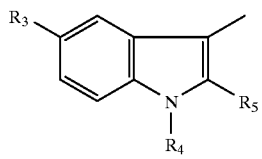

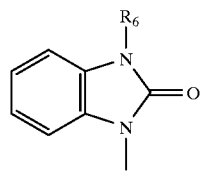

in which $R_3$ is hydrogen or halogen, $R_4$ is hydrogen or $C_{1-3}$ alkyl, $R_5$ is hydrogen or $C_{1-3}$ alkoxy, $R_6$ is hydrogen or linear or branched $C_{1-6}$ alkyl;

Y is a group of formula —$OR_7$ or $NHR_7$, wherein $R_7$ is $C_{1-3}$ alkyl, aryl or aralkly;

R is hydrogen, phenyl, hydroxy, benzyloxy, methylthiomethyl, 3-indolyl, methoxycarbonyl or carbamoyl;

wherein a compound of formula VI

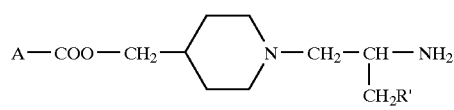

wherein A is as defined hereinabove and R' is hydrogen, phenyl, methylthiomethyl or indolyl, is reacted with isocyanates of formula $R_7$NCO, where $R_7$ is as defined hereinabove, in a polar or non-polar solvent at a temperature ranging from 0° C. to the reflux temperature of the solvent.

6. A process for the preparation of compounds of formula I

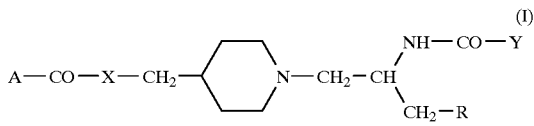

wherein
A is a group selected from
substituted phenyl of structure

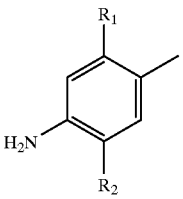

in which $R_1$ is $C_{1-3}$ alkoxy and $R_2$ is halogen; or bi- or tricyclic heterocycle selected from

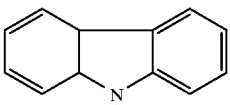

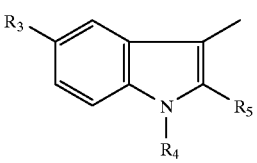

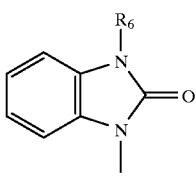

in which $R_3$ is hydrogen or halogen, $R_4$ is hydrogen or $C_{1-3}$ alkyl, $R_5$ is hydrogen or $C_{1-3}$ alkoxy, $R_6$ is hydrogen or linear or branched $C_{1-6}$ alkyl;

X is oxygen or NH;

Y is a group of formula —$OR_7$ or $NHR_7$, wherein $R_7$ is $C_{1-3}$ alkyl, aryl or aralkly;

R is hydrogen, phenyl, hydroxy, benzyloxy, methylthionmethyl, 3-indolyl, methoxycarbonyl or carbamoyl;

wherein a compound of formula (VI)

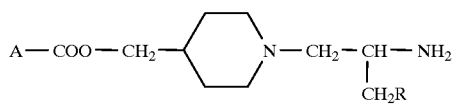
(VI)

wherein A and R are defined hereinabove is reacted with chloroformate of formula $R_7$ OCOCl, wherein $R_7$ is as defined hereinabove, in an inert solvent and in the presence of an acid acceptor at a temperature ranging from 0° C. to the reflux temperature of the solvent.

7. A process for the preparation of compounds of formula I

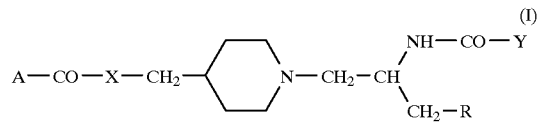
(I)

wherein
A is a group selected from
substituted phenyl of structure

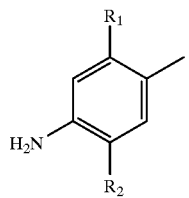
(a)

in which $R_1$ is $C_{1-3}$ alkoxy and $R_2$ is halogen; or bi- or tricyclic heterocycle selected from

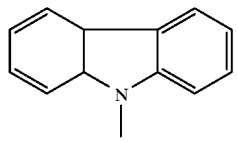
(b)

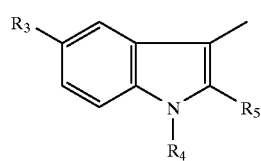
(c)

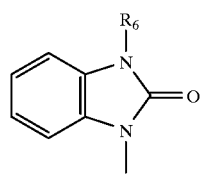
(d)

in which $R_3$ is hydrogen or halogen, $R_4$ is hydrogen or $C_{1-3}$ alkyl, $R_5$ is hydrogen or $C_{1-3}$ alkoxy, $R_6$ is hydrogen or linear or branched $C_{1-6}$ alkyl;
X is oxygen or NH;

Y is a group of formula —$OR_7$ or $NHR_7$, wherein $R_7$ is $C_{1-3}$ alkyl, aryl or aralkly;

R is hydrogen, phenyl, hydroxy, benzyloxy, methylthionmethyl, 3-indolyl, methoxycarbonyl or carbamoyl;

wherein a compound of formula (VI)

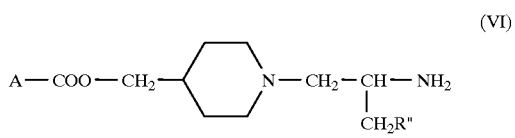
(VI)

wherein A is as defined hereinabove and R" is hydroxy, which is obtained from its precursor benzyloxy, is reacted with an isocyanate of formula $R_7$ NCO or a chloroformate of formula $R_7$ OCOCl, wherein $R_7$ is as defined above, by reduction process with hydrogen in the presence of pd/C.

8. A process for the preparation of compounds of formula I

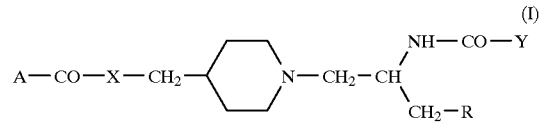
(I)

wherein
A is a group selected from
substituted phenyl of structure

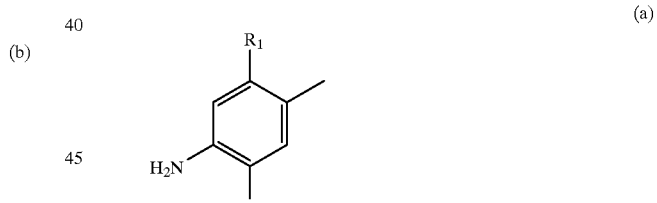
(a)

in which $R_1$ is $C_{1-3}$ alkoxy and $R_2$ is halogen; or bi- or tricyclic heterocycle selected from

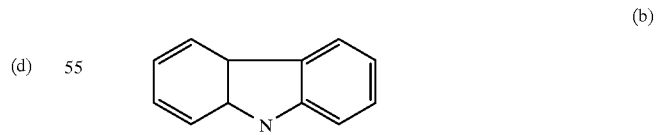
(b)

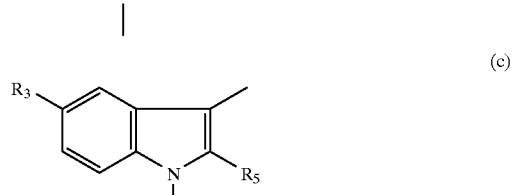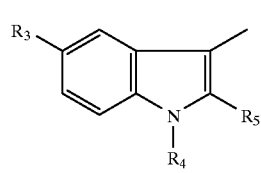
(c)

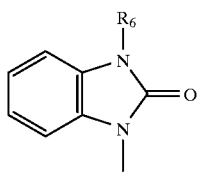

in which $R_3$ is hydrogen or halogen, $R_4$ is hydrogen or $C_{1-3}$ alkyl, $R_5$ is hydrogen or $C_{1-3}$ alkoxy, $R_6$ is hydrogen or linear or branched $C_{1-6}$ alkyl;

X is oxygen or NH;

Y is a group of formula —$OR_7$ or $NHR_7$, wherein $R_7$ is $C_{1-3}$ alkyl, aryl or aralkly;

R is hydrogen, phenyl, hydroxy, benzyloxy, methylthionmethyl, 3-indolyl, methoxycarbonyl or carbamoyl;

wherein a compound of formula (VI)

$$A-COO-CH_2- \text{(piperidine)} -N-CH_2-CH(CH_2R''')-NH_2 \quad (VI)$$

wherein A is as defined hereinabove and R''' is carbamoyl, which is obtained from its precursor alkoxy carbonyl, is reacted with an isocyanate of formula $R_7$ NCO or a chloroformate of formula $R_7$ OCOCl, wherein $R_7$ is as defined hereinafter, by ammonolysis process with gaseous ammonia in a protic or aprotic solvent at a temperature ranging between about 0° C. to about 30° C.

* * * * *